(12) United States Patent
Fahn et al.

(10) Patent No.: US 10,154,927 B2
(45) Date of Patent: Dec. 18, 2018

(54) EAR WAX REMOVAL DEVICE AND METHODS THEREOF

(71) Applicant: WONDERTIP MEDICAL LTD., Herzliya (IL)

(72) Inventors: Miri Fahn, Tel-Aviv (IL); Amir Kraitzer, Herzelia (IL)

(73) Assignee: EARWAYS MEDICAL LTD., Rosh Ha'Ayin (IL)

( * ) Notice: Subject to any disclaimer, the term of this patent is extended or adjusted under 35 U.S.C. 154(b) by 237 days.

(21) Appl. No.: 14/408,000

(22) PCT Filed: Jun. 13, 2013

(86) PCT No.: PCT/IL2013/050511
§ 371 (c)(1),
(2) Date: Dec. 15, 2014

(87) PCT Pub. No.: WO2013/186781
PCT Pub. Date: Dec. 19, 2013

(65) Prior Publication Data
US 2015/0142029 A1    May 21, 2015

Related U.S. Application Data

(60) Provisional application No. 61/659,523, filed on Jun. 14, 2012.

(51) Int. Cl.
*A61F 11/00*    (2006.01)
(52) U.S. Cl.
CPC .................................. *A61F 11/006* (2013.01)

(58) Field of Classification Search
CPC ..... A61F 11/006; A61F 11/00; A61M 1/0023; A61B 17/24; A61B 2017/00685
(Continued)

(56) References Cited

U.S. PATENT DOCUMENTS 3,422,186 A    1/1969   Sasmor
3,923,061 A    12/1975  Rossignol
(Continued)

FOREIGN PATENT DOCUMENTS

CN    2693206 Y    4/2005
CN    2805725 Y    8/2006
(Continued)

OTHER PUBLICATIONS

International Search Report of International Application No. PCT/IL2013/050511 dated Oct. 13, 2013.
(Continued)

*Primary Examiner* — Robert Lynch
*Assistant Examiner* — Lindsey Bachman
(74) *Attorney, Agent, or Firm* — M&B IP Analysts, LLC.

(57) ABSTRACT

The present invention provides a cerumen removal apparatus for mechanically removing cerumen from an ear canal, comprising: a device body having a distal end and a proximal end interconnected by a main longitudinal axis; said distal end comprising at least one collector head for amassing said cerumen; said proximal end comprising at least one rotating mechanism adapted to rotate said at least one collector head; wherein said rotation of said collector head amasses said cerumen and removes said cerumen from said ear canal.

3 Claims, 14 Drawing Sheets

(58) Field of Classification Search
USPC .................................................. 606/161–162
See application file for complete search history.

(56) References Cited

U.S. PATENT DOCUMENTS

| | | | |
|---|---|---|---|
| 4,895,875 A | 1/1990 | Winston | |
| 5,296,472 A | 3/1994 | Sanchez et al. | |
| 5,380,711 A | 1/1995 | Sanchez et al. | |
| 5,390,663 A | 2/1995 | Schaefer | |
| 5,480,658 A | 1/1996 | Melman | |
| 5,490,859 A * | 2/1996 | Mische | A61B 17/320725 606/159 |
| 5,888,199 A | 3/1999 | Karell et al. | |
| 6,152,940 A | 11/2000 | Carter | |
| 6,155,987 A | 12/2000 | Scherl | |
| 6,187,021 B1 * | 2/2001 | Wim | A61F 11/006 606/161 |
| 6,264,664 B1 * | 7/2001 | Avellanet | A61B 17/221 606/1 |
| 6,406,484 B1 | 6/2002 | Lang | |
| 6,417,179 B1 | 7/2002 | Burkhart et al. | |
| 7,332,463 B2 | 2/2008 | Greenberg | |
| 7,500,981 B1 * | 3/2009 | Jubrail | A61F 11/006 606/162 |
| 7,658,745 B2 | 2/2010 | Olson | |
| 7,875,267 B2 | 1/2011 | Okajima et al. | |
| 8,062,216 B2 | 11/2011 | Raghuprasad | |
| 2003/0187469 A1 * | 10/2003 | Olson | A61F 11/006 606/162 |
| 2004/0126436 A1 | 7/2004 | Cagle et al. | |
| 2006/0085018 A1 | 4/2006 | Clevenger | |
| 2006/0253087 A1 | 11/2006 | Vlodaver et al. | |
| 2006/0287656 A1 | 12/2006 | Brown et al. | |
| 2007/0009368 A1 | 1/2007 | Yang | |
| 2008/0142385 A1 | 6/2008 | Stein et al. | |
| 2008/0234602 A1 * | 9/2008 | Oostman | A61B 10/0266 600/564 |
| 2010/0121363 A1 | 5/2010 | Huttner et al. | |
| 2010/0137814 A1 | 6/2010 | Chew | |
| 2010/0312198 A1 | 12/2010 | Guidi | |
| 2011/0015489 A1 | 1/2011 | Raghuprasad | |
| 2011/0066172 A1 * | 3/2011 | Silverstein | A61F 11/006 606/162 |
| 2011/0166421 A1 | 7/2011 | Katiraei | |
| 2012/0296355 A1 | 11/2012 | Burres | |
| 2013/0304103 A1 | 11/2013 | Burres | |
| 2016/0302973 A1 | 10/2016 | Kraitzer et al. | |

FOREIGN PATENT DOCUMENTS

| | | | | |
|---|---|---|---|---|
| CN | 201350157 Y | 11/2009 | | |
| CN | 101632612 A | 1/2010 | | |
| CN | 201426803 Y | 3/2010 | | |
| CN | 201481653 | 5/2010 | | |
| CN | 201481653 U | 5/2010 | | |
| CN | 201654722 U | 11/2010 | | |
| CN | 201719442 U | 1/2011 | | |
| CN | 201759743 U | 3/2011 | | |
| CN | 201894700 U | 7/2011 | | |
| EP | 2412394 B1 | 2/2013 | | |
| FR | 2916135 A1 | 11/2008 | | |
| GB | 2520047 A | 5/2015 | | |
| JP | 2011-36605 A | 2/2011 | | |
| JP | 2011-115346 A | 6/2011 | | |
| JP | 2011115346 A | * 6/2011 | ............... A47K 7/00 |
| JP | 2011-229610 A | 11/2011 | | |
| JP | 2012-30028 A | 2/2012 | | |
| KR | 10-2010-0052442 A | 5/2010 | | |
| KR | 2011017792 | 2/2011 | | |
| KR | 20110017792 A | 2/2011 | | |
| WO | 2009063978 A1 | 5/2009 | | |
| WO | WO-2009/063978 | 5/2009 | | |
| WO | WO2009/063978 | * 5/2009 | ............... A47K 7/00 |
| WO | 2010/017100 A1 | 2/2010 | | |
| WO | 2011/085155 A2 | 7/2011 | | |
| WO | 2012023409 A1 | 2/2012 | | |
| WO | 2012158382 A1 | 11/2012 | | |

OTHER PUBLICATIONS

Jan. 28, 2016 International Search Report issued in International Patent Application No. EP 13804457.
Oct. 13, 2013 International Search Report issued in International Patent Application No. PCT/IL2013/050511.
Notification Before Refusal dated May 22, 2018 for Israeli Patent Application No. 236240, issued from the Israel Patent Office.
"Earway TM PRO Tutorial", Earways Medical, Jun. 18, 2017, retrieved from the internet Aug. 23, 2018, https://www.youtube.com/watch?v=AlmzbJHPLvc.
The International Search Report and the Written Opinion for PCT/IB2018/051965, ISA/US, Alexandria, VA, dated Jul. 16, 2018.

* cited by examiner

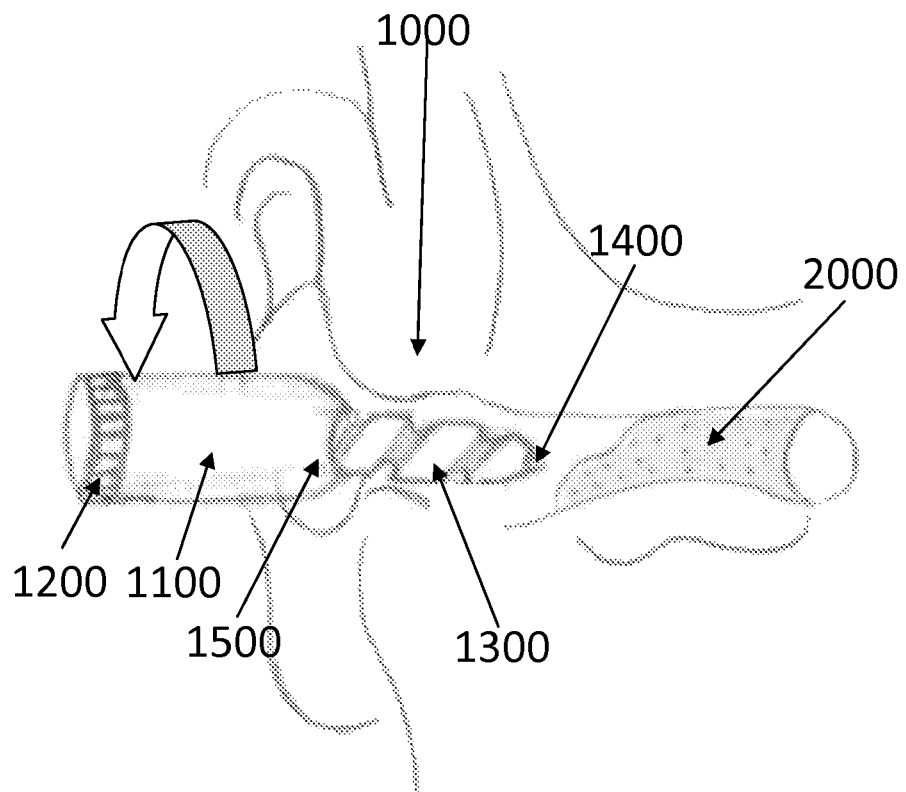
Fig. 3A
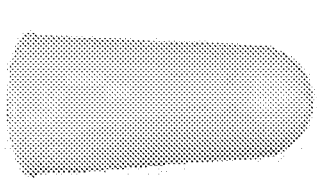 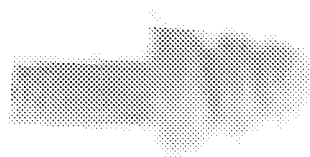 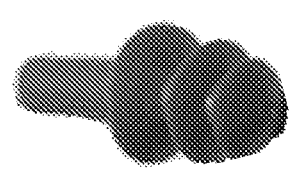
Fig. 3B  Fig. 3C  Fig. 3D

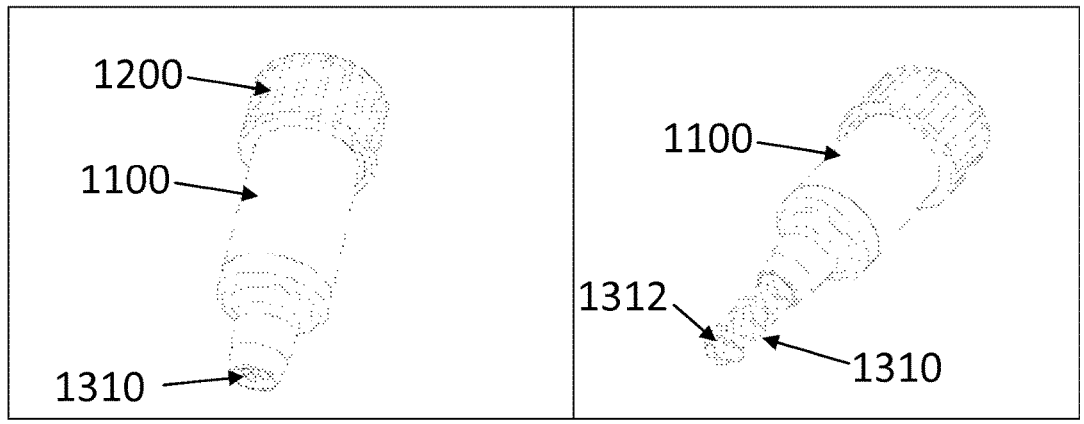
Fig. 6A                    Fig. 6B
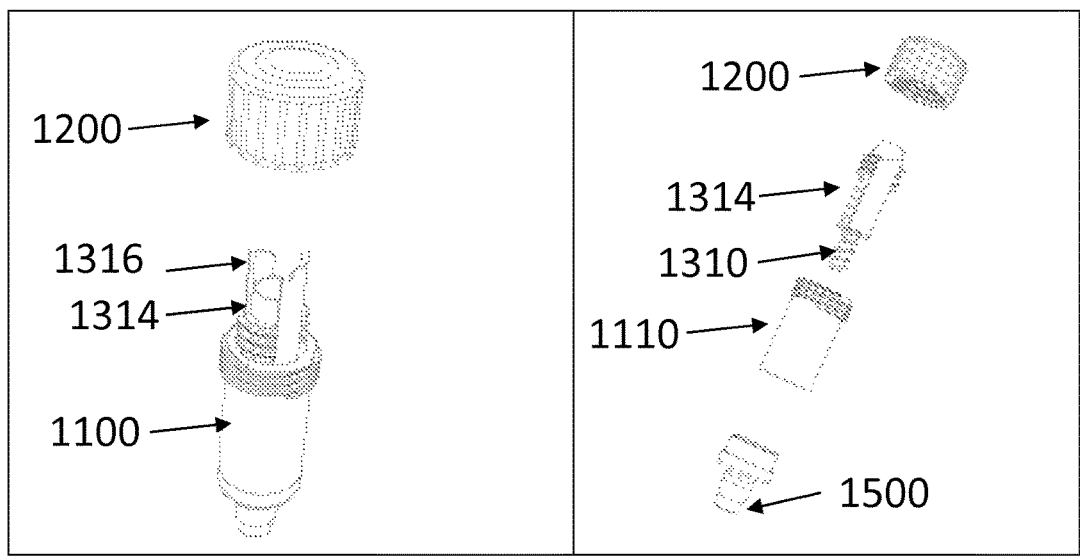
Fig. 6C                    Fig. 6D

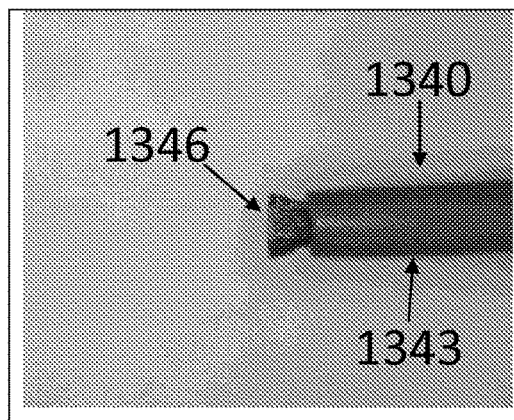 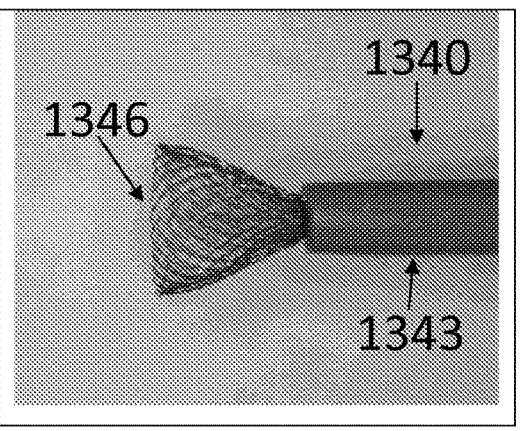
Fig. 8A  Fig. 8B
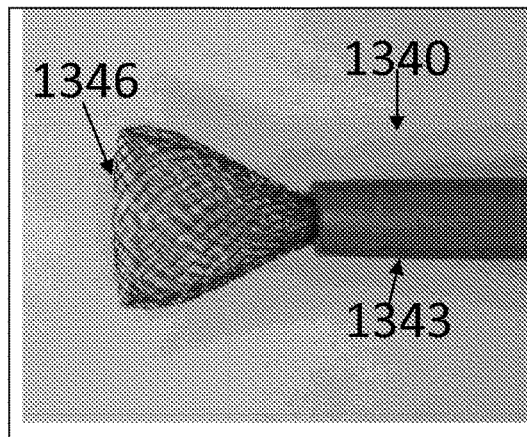 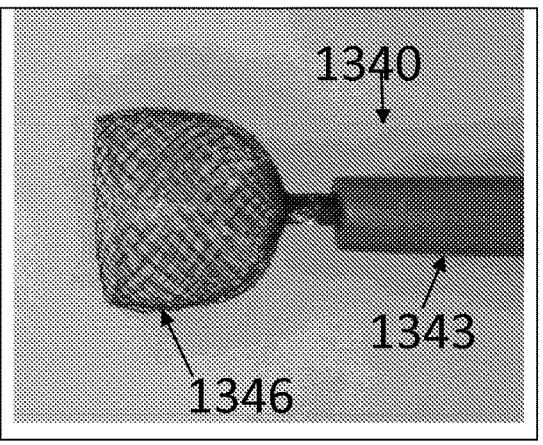
Fig. 8C  Fig. 8D

1350

1355

_EAR WAX REMOVAL DEVICE AND METHODS THEREOF_

CROSS-REFERENCE TO RELATED APPLICATIONS

This application is a National Phase Application of PCT International Application No. PCT/IL2013/050511, International Filing Date Jun. 13, 2013, claiming the benefit of U.S. Provisional Application No. 61/659,523, filed Jun. 14, 2012, which is hereby incorporated by reference.

FIELD OF THE INVENTION

The invention relates to ear wax removal or cerumen impaction relief.

BACKGROUND OF THE INVENTION

Ear wax (cerumen) build-up and impaction in the external ear canal is a common problems faced by primary care physicians such as family practitioners, pediatricians and internists. Cerumen impaction is the presence of obstructing masses of earwax that block the ear canal. Cerumen accumulation can affect up to 6% of the general population and a much higher percentage of older people and people with cognitive impairment. In the US, cerumen accumulation leads to 12 million patient clinic visits and 8 million cerumen removal procedures annually.

In most cases of cerumen impaction, the removal is done by an Ear, Nose and Throat (ENT) doctor who usually removes the cerumen under vaccum, with a curette, or by water irrigation using a syringe. Each approach is associated with risks and benefits. Using a curette allows a clinician to view the procedure and safely remove the cerumen while the lack of water lowers infection risk. However, using a curette requires considerable skill.

Irrigation or "syringing" is a standard method of wax removal and approximately 150,000 ears are irrigated each week in the US. Irrigation, however, involves insertion of liquids using high pressure that might damage the eardrum (Tympanic membrane).

Ear care products for home use include wax softeners or Q-tips, which have very low effectiveness and sometimes involve safety issues. Softeners are often sufficient to treat mild cases of impacted cerumen, as well as reducing the need to be removed by a specialist in some cases. Wax softeners usually used to soften the wax in the ear are baby oil, glycerin, mineral oil, glycerol, olive oil, almond oil, hydrogen peroxide, docusate sodium (dioctyl sodium sulphosuccinate), dichlorobenzene, and carbamide peroxide. Hydrogen peroxide and 10% solution of sodium bicarbonate were found as effective means of removing or softening cerumen.

Current clinical practice for removing cerumen depends heavily on specialized clinicians such as ENT (ear, nose and throat) doctors. Home use products such as earwax softeners do not remove cerumen in the state of impaction but can be useful when used in conjunction with treatment by a ENT doctor or by a general practitioner (either by using irrigation, curette, vacuum, etc.).

Therefore, there is a long-felt need for a means and method for safe and mechanical removal of cerumen which can be carried out in its entirety without a clinician. Moreover, there is a need to simplify the procedure for general practitioners in order reduce the costs of and burden on ENT doctors.

SUMMARY OF THE INVENTION

It is an object of the present invention to disclose an apparatus for and method for mechanically removing impacted cerumen from the ear.

It is another object of the present invention to disclose a cerumen removal apparatus for mechanically removing cerumen from an ear canal, comprising: a device body having a distal end and a proximal end interconnected by a main longitudinal axis; said distal end comprising at least one collector head for amassing said cerumen; said proximal end comprising at least one rotating mechanism adapted to rotate said at least one collector head; wherein said rotation of said collector head amasses said cerumen and removes said cerumen from said ear canal.

It is another object of the present invention to disclose the apparatus as defined above, wherein said device body comprises at least one reservoir, in fluid communication with said at least one collector head, said reservoir containing cerumen softening liquid, adapted to dispense said cerumen softening liquid within said ear canal.

It is another object of the present invention to disclose the apparatus as defined above, wherein said reservoir is allocated within at least one selected from a group consisting of said collector head, said device body, a fluidly connected container emplaced above the level of the ear canal and any combination thereof.

It is another object of the present invention to disclose the apparatus as defined above, wherein said amassing occurs simultaneously with the dispensing of said softening liquid.

It is another object of the present invention to disclose the apparatus as defined above, wherein said amassing occurs after said liquid is dispensed.

It is another object of the present invention to disclose the apparatus as defined above, wherein said collector head is adapted to be movable along said main longitudinal axis, such that said collector head is extendable from said device body.

It is another object of the present invention to disclose the apparatus as defined above, wherein said collector head is adapted to be reversibly movable along said main longitudinal axis, such that said collector head is extendable from said device body and retractable into said device body.

It is another object of the present invention to disclose the apparatus as defined above, wherein said apparatus is removable from said ear canal in a configuration selected from a group consisting of: with said collector head at least partially extended from said device body, and with said collector head retracted into said device body.

It is another object of the present invention to disclose the apparatus as defined above, additionally comprising a retraction mechanism adapted to enable retraction of said collector head into said device body.

It is another object of the present invention to disclose the apparatus as defined above, wherein said retraction mechanism is connected to at least one of a group consisting of said rotating mechanism and said device body via a means selected from a group consisting of a pullable cable, a pullable wire, a rotatable cable, a collapsible shaft, a rotatable shaft, a direct coupling and any combination thereof.

It is another object of the present invention to disclose the apparatus as defined above, wherein said collector head is connected to said rotating mechanism via a means selected from a group consisting of a cable, a wire, a shaft, a direct coupling and any combination thereof, It is another object of the present invention to disclose the apparatus as defined above, wherein said shaft is adapted to change shape in a manner selected from a group consisting of deform, bend, twist, rotate and any combination thereof so as to follow the tortuosity of said ear canal.

It is another object of the present invention to disclose the apparatus as defined above, wherein said shaft comprises a flexible section, said flexible section comprising at least one of a group consisting of accordion pleating, a spiral spring, flexible material, a plurality of hingedly connected segments and any combination thereof.

It is another object of the present invention to disclose the apparatus as defined above, wherein said collector head is adapted to change shape in a manner selected from a group consisting of deform, bend, twist, rotate and any combination thereof so as to follow the tortuosity of said ear canal.

It is another object of the present invention to disclose the apparatus as defined above, wherein said collector head comprises a flexible section, said flexible section comprising at least one of a group consisting of accordion pleating, a spiral spring, flexible material, a plurality of hingedly connected segments and any combination thereof.

It is another object of the present invention to disclose the apparatus as defined above, wherein said accordion pleating is arranged in a manner selected from a group consisting of a plurality of substantially straight, substantially parallel rows, a spiral, and any combination thereof.

It is another object of the present invention to disclose the apparatus as defined above, wherein each said hinged connection is adapted to enable bending of said shaft in at least one direction, thereby enabling said shaft to follow the tortuosity of said ear canal.

It is another object of the present invention to disclose the apparatus as defined above, wherein said hinged connection is selected from a member of a group consisting of a segment comprised of thinner material, a segment comprised of a material of greater flexibility than the connected segments, and any combination thereof.

It is another object of the present invention to disclose the apparatus as defined above, wherein rotational force is applied to said collector head by said rotating mechanism.

It is another object of the present invention to disclose the apparatus as defined above, wherein said collector head comprises an Archimedes screw.

It is another object of the present invention to disclose the apparatus as defined above, wherein the distal end of said Archimedes screw comprises at least one aperture; said aperture fluidly connected to said reservoir, said aperture adapted to enable fluid to flow from said reservoir into said ear canal.

It is another object of the present invention to disclose the apparatus as defined above, wherein said Archimedes screw is comprised of soft material, such that said Archimedes screw can deform to follow the tortuosity of said ear canal.

It is another object of the present invention to disclose the apparatus as defined above, wherein said soft material is selected from a group consisting of silicone, fiber mesh, cellulose, polyurethane, polyethylene, polyamide, polypropylene, and any combination thereof.

It is another object of the present invention to disclose the apparatus as defined above, wherein said Archimedes screw comprises a plurality of hingedly connected segments, such that said Archimedes screw can deform to follow the tortuosity of said ear canal.

It is another object of the present invention to disclose the apparatus as defined above, wherein said Archimedes screw comprises a plurality of segments, said segments connected via a hingedly connected shaft, such that said Archimedes screw can deform to follow the tortuosity of said ear canal.

It is another object of the present invention to disclose the apparatus as defined above, wherein said collector head comprises a milling bit; said milling bit comprising a proximal end and a distal end, wherein said proximal end is substantially cylindrical and said distal end is shaped substantially as the frustum of a cone; said distal end and at least a portion of said proximal end being characterized by at least one spiral groove.

It is another object of the present invention to disclose the apparatus as defined above, wherein said distal end of said milling bit comprises at least one aperture in fluid connection with said reservoir, said aperture adapted to enable fluid to flow from said reservoir into said ear canal.

It is another object of the present invention to disclose the apparatus as defined above, wherein said milling bit is comprised of soft material, such that said milling bit can deform to follow the tortuosity of said ear canal.

It is another object of the present invention to disclose the apparatus as defined above, wherein said soft material is selected from a group consisting of silicone, fiber mesh, cellulose, polyurethane, polyethylene, polyamide, polypropylene, and any combination thereof.

It is another object of the present invention to disclose the apparatus as defined above, wherein said milling bit comprises a plurality of hingedly connected segments, such that said milling bit can deform to follow the tortuosity of said ear canal.

It is another object of the present invention to disclose the apparatus as defined above, wherein said milling bit comprises a plurality of segments, said segments connected via a hingedly connected shaft, such that said milling bit can deform to follow the tortuosity of said ear canal.

It is another object of the present invention to disclose the apparatus as defined above, wherein said collector head comprises a plurality of fibers braided into a form which, at least when fully extended, resembles a basket, said collector is characterized by a proximal end and a distal end, said proximal end comprising a shaft, said distal end comprising said braided basket; said braided basket is characterized by at least two positions, a retracted position wherein said braided basket is substantially contained within said shaft and an extended position wherein at least a portion of said braided basket extends beyond the distal end of said shaft.

It is another object of the present invention to disclose the apparatus as defined above, wherein said shaft is fluidly connected to said reservoir.

It is another object of the present invention to disclose the apparatus as defined above, wherein said braided basket is reversibly transformable between said retracted position and said extended position.

It is another object of the present invention to disclose the apparatus as defined above, wherein said rotation of said rotating mechanism reversibly transforms said braided basket from said retracted position to said extended position.

It is another object of the present invention to disclose the apparatus as defined above, wherein retraction of said braided basket into said shaft occurs either before or during removal of said apparatus from said ear canal.

It is another object of the present invention to disclose the apparatus as defined above, wherein said shaft is at least partially an open bore shaft.

It is another object of the present invention to disclose the apparatus as defined above, wherein said braided basket is comprised of at least one elastic fiber.

It is another object of the present invention to disclose the apparatus as defined above, wherein said at least one elastic fiber is made of a material selected from a group consisting of steel, nickel-titanium, beta-titanium, plastic and any combination thereof.

It is another object of the present invention to disclose the apparatus as defined above, wherein said elastic fiber comprises at least one filament.

It is another object of the present invention to disclose the apparatus as defined above, wherein said elastic fiber comprises at least one selected from a group consisting of fibers wound without a core, fibers wound around a core, braided fibers and any combination thereof.

It is another object of the present invention to disclose the apparatus as defined above, wherein at least one of said at least one elastic fiber is coated.

It is another object of the present invention to disclose the apparatus as defined above, wherein said coating is comprised of at least one selected from a group consisting of metal, plastic, Teflon, natural fibers, polyester, rayon, nylon, woven material, non-woven material and any combination thereof.

It is another object of the present invention to disclose the apparatus as defined above, wherein said collector head comprises a sponge.

It is another object of the present invention to disclose the apparatus as defined above, wherein said sponge is fluidly connected to said reservoir, said sponge is adapted to allow fluid selected from cerumen softening fluid, softened cerumen and any combination thereof to pass therethrough.

It is another object of the present invention to disclose the apparatus as defined above, wherein the shape of said sponge is selected from a group consisting of substantially cylindrical in shape, substantially shaped as a frustum of a cone, substantially conic, and any combination thereof.

It is another object of the present invention to disclose the apparatus as defined above, wherein said sponge is comprised of at least one selected from a group consisting of cellulose, polyurethane, polyethylene, polyamide, polypropylene and any combination thereof.

It is another object of the present invention to disclose the apparatus as defined above, wherein said collector head comprises a thin foil, said collector head further comprises a proximal end and a distal end, said proximal end comprising a shaft and said distal end comprising said thin foil.

It is another object of the present invention to disclose the apparatus as defined above, wherein said thin foil is formed into the shape of the frustum of a cone.

It is another object of the present invention to disclose the apparatus as defined above, wherein the cone comprises at least one longitudinal slit such that said foil comprises at least two longitudinal free edges.

It is another object of the present invention to disclose the apparatus as defined above, wherein said thin foil has a thickness between approximately 0.05 mm thick and approximately 0.5 mm thick.

It is another object of the present invention to disclose the apparatus as defined above, wherein the material of which said foil is comprised is selected from a group consisting of: polyimide, polyvinyl chloride (PVC), Polyethylene (PE), polypropylene (PP), Polyether ether ketone (PEEK), laminates of thermoplastic elastomers, thermoplastic plastics and any combination thereof.

It is another object of the present invention to disclose the apparatus as defined above, wherein at least one of said distal end of said foil and the proximal end of said foil further comprises a ring, said ring adapted to plastically deform such that said ring retains its deformed shape at such time as said apparatus is removed from said ear.

It is another object of the present invention to disclose the apparatus as defined above, wherein the material of which said ring is comprised is selected from a group consisting of: polyimide, polyvinyl chloride (PVC), Polyethylene (PE), polypropylene (PP), Polyether ether ketone (PEEK), laminates of thermoplastic elastomers, thermoplastic plastics, metal and any combination thereof.

It is another object of the present invention to disclose the apparatus as defined above, wherein said foil is stiffened with at least one strut, said at least one strut extending in at least one direction selected from a group consisting of: longitudinally along said foil, transversely around said foil, and spirally along said foil.

It is another object of the present invention to disclose the apparatus as defined above, wherein the material of which said at least one strut is comprised is selected from a group consisting of: polyimide, polyvinyl chloride (PVC), PEEK, PE, PP, Polyamid, laminates of thermoplastic elastomers, thermoplastic plastics, metal and any combination thereof.

It is another object of the present invention to disclose the apparatus as defined above, wherein said foil additionally comprises interior face collection/guidance means selected from a group consisting of protrusions, vanes, ridges, and any combination thereof, said guidance means adapted to collect said cerumen and guide said cerumen towards the proximal end of said collector head.

It is another object of the present invention to disclose the apparatus as defined above, wherein minimum height of said collection/guidance means is at its distal end.

It is another object of the present invention to disclose the apparatus as defined above, wherein maximum height of said collection/guidance means is substantially at its proximal end.

It is another object of the present invention to disclose the apparatus as defined above, wherein the material of which said collection/guidance means is comprised is selected from a group consisting of: the foil itself, polyimide, polyvinyl chloride (PVC), PEEK, PE, PP, Polyamid, laminates of thermoplastic elastomers, thermoplastic plastics, metal and any combination thereof.

It is another object of the present invention to disclose the apparatus as defined above, wherein said collector head is formed substantially as a scoop, said scoop having a transverse cross section shaped substantially as a segment of a circle.

It is another object of the present invention to disclose the apparatus as defined above, wherein said segment of a circle is approximately semicircular.

It is another object of the present invention to disclose the apparatus as defined above, wherein said scoop is connected to said device body by a shaft It is another object of the present invention to disclose the apparatus as defined above, wherein said scoop is fluidly connected to said device body.

It is another object of the present invention to disclose the apparatus as defined above, wherein said scoop comprises on its interior face collection/guidance means selected from a group consisting of vanes, ridges, and any combination thereof, said collection/guidance means adapted to collect said cerumen and guide it towards the proximal end of said collector head.

It is another object of the present invention to disclose the apparatus as defined above, wherein minimum height of said collection/guidance means is at its distal end.

It is another object of the present invention to disclose the apparatus as defined above, wherein maximum height of said collection/guidance means is substantially at its proximal end.

It is another object of the present invention to disclose the apparatus as defined above, wherein said collector head is formed substantially as a shovel, said shovel having a transverse cross section shaped substantially as a U.

It is another object of the present invention to disclose the apparatus as defined above, wherein said shovel is connected to said device body by a shaft.

It is another object of the present invention to disclose the apparatus as defined above, wherein said shovel is fluidly connected to said device body.

It is another object of the present invention to disclose the apparatus as defined above, wherein said shovel comprises on its interior face collection/guidance means selected from a group consisting of vanes, ridges, and any combination thereof, said collection/guidance means adapted to guide said cerumen towards the proximal end of said collector head.

It is another object of the present invention to disclose the apparatus as defined above, wherein minimum height of said collection/guidance means is at its distal end.

It is another object of the present invention to disclose the apparatus as defined above, wherein maximum height of said collection/guidance means is substantially at its proximal end.

It is another object of the present invention to disclose the apparatus as defined above, wherein said apparatus is implantable into said ear canal manually or automatically.

It is another object of the present invention to disclose the apparatus as defined above, wherein at least a part of said apparatus is enclosed within a shell.

It is another object of the present invention to disclose the apparatus as defined above, wherein said shell is adapted to be biodegradable, and further wherein said shell is adapted to biodegrade prior to amassing cerumen to said apparatus.

It is another object of the present invention to disclose the apparatus as defined above, wherein said biodegradable shell is comprised of at least one selected from a group consisting of: biodegradable polythene, beeswax, biodegradable polyethylene, biodegradable polypropylene, poly (lactic-co-glycolic acid) (plga), Poly-L-Lactides (plla), Polyglycolide (pga), Poly Lactic-co-Glycolic Acid (PLGA) and any combination thereof.

It is another object of the present invention to disclose the apparatus as defined above, wherein said softening liquid is selected from a group consisting of baby oil, glycerin, mineral oil, glycerol, olive oil, almond oil, hydrogen peroxide, docusate sodium (dioctyl sodium sulphosuccinate), dichlorobenzene, and carbamide peroxide, Hydrogen peroxide, solution of sodium bicarbonate, commercial earwax removal liquid, and any combination thereof.

It is another object of the present invention to disclose the apparatus as defined above, wherein the longitudinal section of said collector head comprises a cylinder; the longitudinal section of the collector head comprises a frustum of a cone.

It is another object of the present invention to disclose the apparatus as defined above, wherein rotation of the knob is adapted to enable collection of said cerumen in a manner selected from a group consisting of: collecting said cerumen without dispensing softening liquid; dispensing said softening liquid followed by collection of said cerumen; dispensing said softening liquid and collecting said cerumen simultaneously; and any combination thereof.

It is another object of the present invention to disclose the apparatus as defined above, wherein said rotating mechanism comprises a decoupling mechanism such that rotation of said rotating mechanism extends the collector head no more than a predetermined amount.

It is another object of the present invention to disclose the apparatus as defined above, wherein, in the device's undeformed configuration, the main longitudinal axis of said spiral spring is substantially collinear with the main longitudinal axis of said collector head.

It is another object of the present invention to disclose the apparatus as defined above, wherein at least a portion of said collector head is comprised of elastic spring-like material adapted to apply radial forces that press said portion of said collector head against the walls of said ear canal.

It is another object of the present invention to disclose a method for mechanically removing cerumen from an ear canal, comprising:
a. providing a cerumen removal apparatus for mechanically removing cerumen from the ear canal, comprising: a device body having a distal end and a proximal end interconnected by a main longitudinal axis; said distal end comprising at least one collector head for amassing said cerumen; said proximal end comprises at least one rotating mechanism to rotate said at least one collector head;
b. emplacing said cerumen removal apparatus in said ear canal;
c. rotating said rotating mechanism, thereby amassing said cerumen; thereby removing said cerumen from said ear canal.

It is another object of the present invention to disclose the method as defined above, additionally comprising a step of providing at least one reservoir, in fluid communication with said at least one collector head, said reservoir containing cerumen softening liquid, said reservoir is for dispensing said cerumen softening liquid within said ear canal.

It is another object of the present invention to disclose the method as defined above, additionally comprising a step of dispensing said cerumen softening liquid within said ear canal.

It is another object of the present invention to disclose the method as defined above, additionally comprising a step of allocating said reservoir within a member of a group consisting of said collector head, said device body, a fluidly connected container emplaced above the level of the ear canal and any combination thereof.

It is another object of the present invention to disclose the method as defined above, wherein said step of amassing occurs simultaneously with the dispensing of said softening liquid.

It is another object of the present invention to disclose the method as defined above, wherein said step of amassing occurs after said liquid is dispensed.

It is another object of the present invention to disclose the method as defined above, additionally comprising a step of moving said collector head along said main longitudinal axis, thereby extending said collector head from said device body.

It is another object of the present invention to disclose the method as defined above, additionally comprising a step of reversibly moving said collector head along said main longitudinal axis, thereby extending said collector head from said device body and retracting said collector head into said device body.

It is another object of the present invention to disclose the method as defined above, additionally comprising a step of removing said apparatus from said ear canal in a configuration selected from a group consisting of: with said collector head at least partially extended from said device body, and with said collector head retracted into said device body.

It is another object of the present invention to disclose the method as defined above, additionally comprising a step of retracting said collector head into said device body by using a retraction mechanism.

It is another object of the present invention to disclose the method as defined above, additionally comprising a step of connecting said retraction mechanism to at least one of a group consisting of said rotating mechanism and said device body via a means selected from a group consisting of a pullable cable, a pullable wire, a rotatable wire, a collapsible shaft, a rotatable shaft, a direct coupling and any combination thereof.

It is another object of the present invention to disclose the method as defined above, additionally comprising a step of connecting said collector head to said rotating mechanism via a means selected from a group consisting of a cable, a wire, a shaft, a direct coupling and any combination thereof.

It is another object of the present invention to disclose the method as defined above, additionally comprising a step of reorienting at least a portion of said shaft by at least one selected from a group consisting of deforming said at least a portion of said shaft, bending said at least a portion of said shaft, twisting said at least a portion of said shaft, rotating said at least a portion of said shaft and any combination thereof so as to follow the tortuosity of said ear canal.

It is another object of the present invention to disclose the method as defined above, additionally comprising a step of comprising said shaft of a flexible section, said flexible section comprising at least one of a group consisting of accordion pleating, a spiral spring, flexible material, a plurality of hingedly connected segments and any combination thereof.

It is another object of the present invention to disclose the method as defined above, additionally comprising a step of reorienting at least a portion of said collector head by at least one selected from a group consisting of deforming said at least a portion of said collector head, bending said at least a portion of said collector head, twisting said at least a portion of said collector head, rotating said at least a portion of said collector head and any combination thereof so as to follow the tortuosity of said ear canal.

It is another object of the present invention to disclose the method as defined above, additionally comprising a step of providing said collector head with a flexible section, said flexible section comprising at least one of a group consisting of accordion pleating, a spiral spring, a flexible material, a plurality of hingedly connected segments and any combination thereof.

It is another object of the present invention to disclose the method as defined above, additionally comprising a step of disposing said accordion pleating in a manner selected from a group consisting of substantially straight, substantially parallel rows, a spiral, and any combination thereof It is another object of the present invention to disclose the method as defined above, additionally comprising a step of connecting said hingedly connected segments via a hinge, each said hinge bending said shaft in at least one direction, said shaft thereby following the tortuosity of said ear canal.

It is another object of the present invention to disclose the method as defined above, additionally comprising a step of comprising said hinged connection of a member selected from a group consisting of a segment comprised of thinner material, a segment comprised of a material of greater flexibility than the connected segments, and any combination thereof.

It is another object of the present invention to disclose the method as defined above, additionally comprising a step of applying rotational force to the collector head by said rotating mechanism.

It is another object of the present invention to disclose the method as defined above, additionally comprising a step of providing said collector head comprising an Archimedes screw.

It is another object of the present invention to disclose the method as defined above, additionally comprising a step of comprising the distal end of said Archimedes screw of at least one aperture; said aperture fluidly connected to said reservoir such that fluid can flow from said reservoir into said ear canal via said aperture.

It is another object of the present invention to disclose the method as defined above, additionally comprising a step of comprising said Archimedes screw of soft material, said Archimedes screw thereby following the tortuosity of said ear canal.

It is another object of the present invention to disclose the method as defined above, additionally comprising a step of selecting said soft material from a group consisting of silicone, fiber mesh, cellulose, polyurethane, polyethylene, polyamide, polypropylene, and any combination thereof.

It is another object of the present invention to disclose the method as defined above, additionally comprising a step of comprising said Archimedes screw of a plurality of hingedly connected segments, said Archimedes screw thereby following the tortuosity of said ear canal.

It is another object of the present invention to disclose the method as defined above, additionally comprising steps of comprising said Archimedes screw of a plurality of segments, connecting said segments via a hingedly connected shaft, said Archimedes screw thereby following the tortuosity of said ear canal.

It is another object of the present invention to disclose the method as defined above, additionally comprising a step of providing said collector head comprising a milling bit; said milling bit comprising a proximal end and a distal end, wherein said proximal end is substantially cylindrical and said distal end is shaped substantially as the frustum of a cone; said distal end and at least a portion of said proximal end being characterized by at least one spiral groove.

It is another object of the present invention to disclose the method as defined above, additionally comprising a step of comprising said distal end of said milling bit of at least one aperture in fluid connection with said reservoir, fluid flowing from said reservoir into said ear canal via said aperture.

It is another object of the present invention to disclose the method as defined above, additionally comprising a step of comprising said milling bit of soft material, said milling bit thereby following the tortuosity of said ear canal.

It is another object of the present invention to disclose the method as defined above, additionally comprising a step of selecting said soft material from a group consisting of silicone, fiber mesh, cellulose, polyurethane, polyethylene, polyamide, polypropylene, and any combination thereof.

It is another object of the present invention to disclose the method as defined above, additionally comprising a step of comprising said milling bit of a plurality of hingedly connected segments, said milling bit thereby following the tortuosity of said ear canal.

It is another object of the present invention to disclose the method as defined above, additionally comprising steps of comprising said milling bit of a plurality of segments, connecting said segments via a hingedly connected shaft, said milling bit thereby following the tortuosity of said ear canal.

It is another object of the present invention to disclose the method as defined above, additionally comprising a step of constructing said collector head of fibers braided into a form which, at least when fully extended, resembles a basket, said collector characterized by a proximal end and a distal end, said proximal end comprising a shaft, said distal end comprising said braided basket; said braided basket is characterized by at least two positions, a retracted position wherein said braided basket is substantially contained within said shaft and an extended position wherein at least a portion of said braided basket extends beyond the distal end of said shaft.

It is another object of the present invention to disclose the method as defined above, additionally comprising a step of providing said shaft fluidly connected to said reservoir.

It is another object of the present invention to disclose the method as defined above, additionally comprising a step of reversibly transforming said braided basket between said retracted position and said extended position.

It is another object of the present invention to disclose the method as defined above, additionally comprising a step of reversibly transforming said braided basket from said retracted position to said extended position by rotating said rotating mechanism.

It is another object of the present invention to disclose the method as defined above, additionally comprising a step of retracting said braided basket into said shaft at least one of before or during removal of said apparatus from said ear canal.

It is another object of the present invention to disclose the method as defined above, additionally comprising a step of providing said shaft as an at least partially an open bore shaft.

It is another object of the present invention to disclose the method as defined above, additionally comprising a step of comprising said braided basket of at least one elastic fiber.

It is another object of the present invention to disclose the method as defined above, additionally comprising a step of making said at least one elastic fiber of a material selected from a group consisting of steel, nickel-titanium, beta-titanium, plastic and any combination thereof.

It is another object of the present invention to disclose the method as defined above, additionally comprising a step of comprising said elastic fiber of at least one filament.

It is another object of the present invention to disclose the method as defined above, additionally comprising a step of comprising said elastic fiber of at least one selected from a group consisting of fibers wound without a core, fibers wound around a core, braided fibers and any combination thereof.

It is another object of the present invention to disclose the method as defined above, additionally comprising a step of coating at least one of said at least one elastic fiber.

It is another object of the present invention to disclose the method as defined above, additionally comprising a step of comprising said coating of at least one selected from a group consisting of metal, plastic, Teflon, natural fibers, polyester, rayon, nylon, woven material, non-woven material and any combination thereof.

It is another object of the present invention to disclose the method as defined above, additionally comprising a step of comprising said collector head of a sponge.

It is another object of the present invention to disclose the method as defined above, additionally comprising a step of fluidly connecting said sponge to said reservoir, fluid selected from cerumen softening fluid, softened cerumen and any combination thereof thereby passing through said sponge.

It is another object of the present invention to disclose the method as defined above, additionally comprising a step of selecting the shape of said sponge from a group consisting of: substantially cylindrical, substantially shaped as a frustum of a cone, substantially conic, and any combination thereof.

It is another object of the present invention to disclose the method as defined above, additionally comprising a step of comprising said sponge of at least one selected from a group consisting of cellulose, polyurethane, polyethylene, polyamide, polypropylene, and any combination thereof.

It is another object of the present invention to disclose the method as defined above, additionally comprising steps of comprising said collector head of a thin foil, said collector head comprising a proximal end and a distal end; comprising said proximal end of a shaft comprising flexible section and comprising said distal end of said thin foil.

It is another object of the present invention to disclose the method as defined above, additionally comprising a step of providing said thin foil in the shape of the frustum of a cone.

It is another object of the present invention to disclose the method as defined above, additionally comprising a step of providing said cone with at least one longitudinal slit such that said foil comprises at least two longitudinal free edges.

It is another object of the present invention to disclose the method as defined above, additionally comprising a step of providing said thin foil in the range of approximately 0.05 mm thick and approximately 0.5 mm thick.

It is another object of the present invention to disclose the method as defined above, additionally comprising a step of providing said thin foil approximately 0.1 mm thick It is another object of the present invention to disclose the method as defined above, additionally comprising a step of selecting the material of which said foil is comprised from a group consisting of: polyimide, polyvinyl chloride (PVC), Polyethylene (PE), polypropylene (PP), Polyether ether ketone (PEEK), laminates of thermoplastic elastomers, thermoplastic plastics and any combination thereof.

It is another object of the present invention to disclose the method as defined above, additionally comprising steps of comprising a ring at at least one of said distal end of said foil and the proximal end of said foil; and plastically deforming said ring, thereby retaining said ring in its deformed shape at such time as said apparatus is removed from said ear.

It is another object of the present invention to disclose the method as defined above, additionally comprising a step of comprising said ring of material selected from a group consisting of: polyimide, polyvinyl chloride (PVC), Polyethylene (PE), polypropylene (PP), Polyether ether ketone (PEEK), laminates of thermoplastic elastomers, thermoplastic plastics, metal and any combination thereof.

It is another object of the present invention to disclose the method as defined above, additionally comprising a step of stiffening said foil with at least one strut, said at least one strut extending in at least one direction selected from a group consisting of: longitudinally along said foil, transversely around said foil, and spirally along said foil.

It is another object of the present invention to disclose the method as defined above, additionally comprising a step of selecting the material of which said at least one strut is comprised from a group consisting of: polyimide, polyvinyl chloride (PVC), PEEK, PE, PP, Polyamid, laminates of thermoplastic elastomers, thermoplastic plastics, metal and any combination thereof.

It is another object of the present invention to disclose the method as defined above, additionally comprising a step of comprising on the interior face of said foil collection/guidance means selected from a group consisting of protrusions, vanes, ridges, and any combination thereof, said guidance means enabled to collect said cerumen and guide said cerumen towards the proximal end of said collector head.

It is another object of the present invention to disclose the method as defined above, additionally comprising a step of shaping said collection/guidance means such that minimum height of said collection/guidance means is at its distal end.

It is another object of the present invention to disclose the method as defined above, additionally comprising a step of shaping said collection/guidance means such that maximum height of said collection/guidance means is substantially at its proximal end.

It is another object of the present invention to disclose the method as defined above, additionally comprising a step of selecting the material of which said at least one strut is comprised from a group consisting of: polyimide, polyvinyl chloride (PVC), PEEK, PE, PP, Polyamid, laminates of thermoplastic elastomers, thermoplastic plastics, metal and any combination thereof.

It is another object of the present invention to disclose the method as defined above, additionally comprising a step of selecting said collector head formed substantially as a scoop, said scoop having a transverse cross section shaped substantially as a segment of a circle.

It is another object of the present invention to disclose the method as defined above, additionally comprising a step of selecting said segment of a circle to be approximately semicircular.

It is another object of the present invention to disclose the method as defined above, additionally comprising a step of connecting said scoop to said device body by a shaft.

It is another object of the present invention to disclose the method as defined above, additionally comprising a step of providing said scoop fluidly connected to said device body.

It is another object of the present invention to disclose the method as defined above, additionally comprising a step of comprising on the interior face of said scoop collection/guidance means selected from a group consisting of vanes, ridges, and any combination thereof, said collection/guidance means enabled to guide said cerumen towards the proximal end of said collector head.

It is another object of the present invention to disclose the method as defined above, additionally comprising a step of shaping said collection/guidance means such that minimum height of said collection/guidance means is at its distal end.

It is another object of the present invention to disclose the method as defined above, additionally comprising a step of shaping said collection/guidance means such that maximum height of said collection/guidance means is substantially at its proximal end.

It is another object of the present invention to disclose the method as defined above, additionally comprising a step of providing said collector head formed substantially as a shovel, said shovel having a transverse cross section shaped substantially as a U.

It is another object of the present invention to disclose the method as defined above, additionally comprising a step of connecting said shovel to said device body by a shaft.

It is another object of the present invention to disclose the method as defined above, additionally comprising a step of providing said shovel fluidly connected to said device body.

It is another object of the present invention to disclose the method as defined above, additionally comprising a step of comprising on the interior face of said shovel guidance means selected from a group consisting of vanes, ridges, grooves and any combination thereof, said guidance means enabled to guide said cerumen towards the proximal end of said collector head.

It is another object of the present invention to disclose the method as defined above, additionally comprising a step of shaping said collection/guidance means such that minimum height of said collection/guidance means is at its distal end.

It is another object of the present invention to disclose the method as defined above, additionally comprising a step of shaping said collection/guidance means such that maximum height of said collection/guidance means is substantially at its proximal end.

It is another object of the present invention to disclose the method as defined above, additionally comprising a step of implanting said apparatus into said ear canal manually or automatically.

It is another object of the present invention to disclose the method as defined above, additionally comprising a step of enclosing at least a part of said apparatus within a shell.

It is another object of the present invention to disclose the method as defined above, additionally comprising a step of providing said shell comprised of biodegradable material, and biodegrading said shell prior to amassing cerumen to said apparatus.

It is another object of the present invention to disclose the method as defined above, additionally comprising a step of comprising said biodegradable shell of at least one selected from a group consisting of: biodegradable polythene, beeswax, biodegradable polyethylene, biodegradable polypropylene, poly(lactic-co-glycolic acid) (plga), Poly-L-Lactides (plla), Polyglycolide (pga), Poly Lactic-co-Glycolic Acid (PLGA) and any combination thereof.

It is another object of the present invention to disclose the method as defined above, additionally comprising a step of selecting said softening liquid from a group consisting of baby oil, glycerin, mineral oil, glycerol, olive oil, almond oil, hydrogen peroxide, docusate sodium (dioctyl sodium sulphosuccinate), dichlorobenzene, and carbamide peroxide, Hydrogen peroxide, 10% solution of sodium bicarbonate, commercial earwax removal liquid, and any combination thereof It is another object of the present invention to disclose the method as defined above, additionally comprising a step of comprising the longitudinal section of said collector head of a cylinder; comprising the longitudinal section of the collector head of a frustum of a cone.

It is another object of the present invention to disclose the method as defined above, additionally comprising a step of collecting said cerumen in a manner selected from a group consisting of: collecting said cerumen without dispensing softening liquid; dispensing said softening liquid followed by collection of said cerumen; dispensing said softening liquid and collecting said cerumen simultaneously; and any combination thereof.

It is another object of the present invention to disclose the method as defined above, additionally comprising a step of decoupling said rotating mechanism, thereby extending said rotating mechanism no more than a predetermined amount.

It is another object of the present invention to disclose the method as defined above, additionally comprising a step of providing said device configured such that, in the device's undeformed configuration, the main longitudinal axis of said spiral spring is substantially collinear with the main longitudinal axis of said collector head.

It is another object of the present invention to disclose the method as defined above, additionally comprising a step of comprising at least a portion of said collector head of elastic spring-like material adapted to apply radial forces that press said portion of said collector head against the walls of said ear canal.

BRIEF DESCRIPTION OF THE FIGURES

In order to better understand the invention and its implementation in practice, a plurality of embodiments will now be described, by way of non-limiting example only, with reference to the accompanying drawings, wherein

FIG. 3A-C schematically illustrates a process of using a device for removing cerumen from the ear and FIG. 3D schematically illustrates designs for the exterior of the part of the device which fits into the ear;

FIGS. 7-11 schematically illustrate embodiments of the collector head;

DETAILED DESCRIPTION OF PREFERRED EMBODIMENTS

Figure 1:
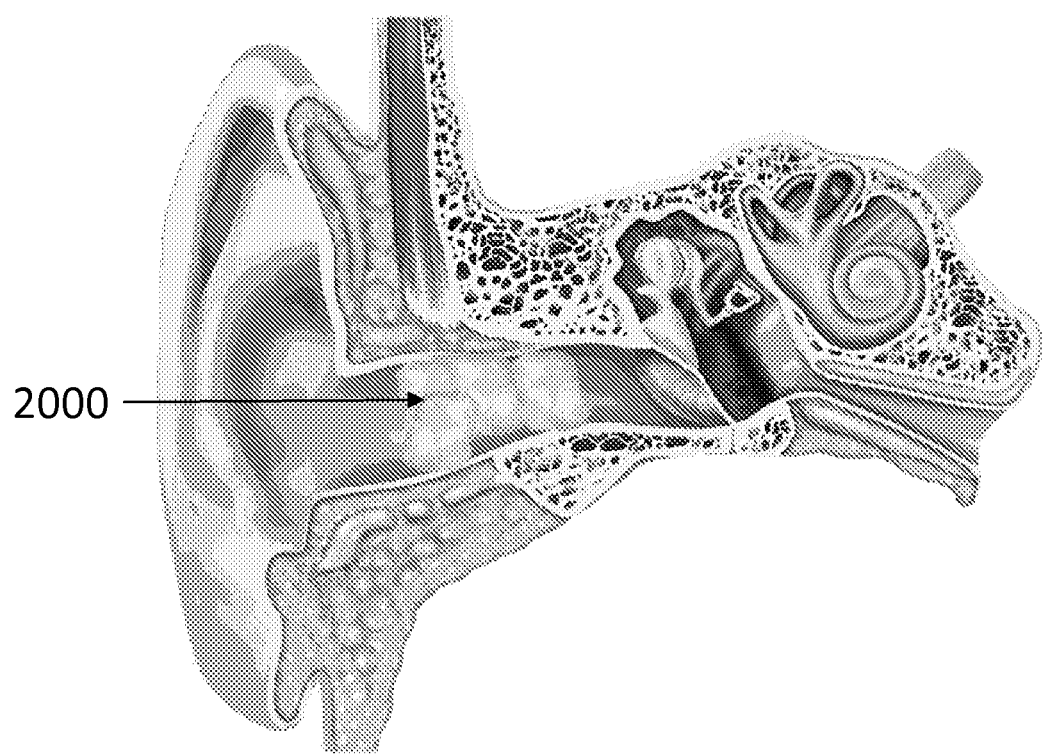
FIG. 1 illustrates the outer ear, showing impacted cerumen in the ear canal.

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a means and method for and method for providing mechanical removal of cerumen from the ear canal.

The term 'approximately' hereinafter refers to within 20% of the value.

The term 'plurality' hereinafter refers to any integer greater than one.

The term 'amass' hereinafter refers to accumulating or assembling a quantity of material.

The term 'distal' hereinafter refers to the part which, in use, is further into the external ear canal.

The term 'proximal' hereinafter refers to the part which, in use, is closer to the exterior of the ear. In a device comprising 2 parts, a first part resting against the external ear and a second part extending into the ear canal, the proximal part is the first part and the distal part is the second part. The proximal end of the distal (second) part is that end of the distal part which is within the first (proximal) part.

The term 'plurality' hereinafter refers to any integer greater than or equal to one.

The term 'hingedly connected' hereinafter refers to a connection which functions as a hinge, such that there exists at least one connecting part, each connecting part linking two connected parts, each connecting part being more flexible than the connected parts it joins, so that each connecting part functions as a hinge, allowing the adjoining connected parts to bend relative to each other in at least one direction.

The term 'main longitudinal axis' refers hereinafter to the axis extending along the long axis of the device. According to one embodiment, said device can be either a linear or a non linear device.

The term 'deform' refers hereinafter to any mechanical deformation e.g., bending, stretching, compression, twisting and any combination of these.

The term 'plastically deform' or 'plastic deformation' refers hereinafter to any permanent mechanical deformation.

The term 'braided basket' refers hereinafter to a plurality of fibers braided into a form which, when fully extended, resembles a basket. The action of the basket is to expand and collect cerumen during expansion and then capture it during contraction.

The term 'accordion pleat' refers hereinafter to substantially evenly spaced, substantially parallel folds. The accordion pleating can form, for non-limiting example, a series of parallel rows, or a spiral.

The term 'outgoing soft cerumen' or 'soft cerumen' refers hereinafter to any form of cerumen mixture e.g., a paste, a wax, a liquid, or a semi-solid. Typically, the soft cerumen will have high viscosity.

The terms 'all three directions' and 'all three dimensions' refer hereinafter to three directions that form the axes of a three dimensional coordinate system. For non-limiting example, an object whose tip can bend in all three directions can be pointed at any desired point in space.

In the figures hereinbelow, identical numbers refer to similar parts.

Cerumen is a naturally occurring substance that under normal conditions cleans, protects and lubricates the external auditory canal. Cerumen is eliminated by a self-cleaning mechanism which causes it to migrate out of the ear canal, assisted by jaw movement. Excessive ear wax can harden in the ear canal and block the ear.

Cerumen is composed of sheets of corneocytes, originating from the deep and superficial external auditory canal, mixed with glandular secretions whereas keratin accounts for up to 60% of the cerumen plug phenotypes. In FIG. 1, a schematic of the ear canal is shown, containing impacted cerumen (2000).

Cerumen is a relatively hard material. Therefore, in order to simplify its removal it needs to be dissolved or wetted to eventually become a soft paste-like material. In some embodiments, the current invention combines the effects of liquid immersion, cerumen soaking, and mechanical collection of the cerumen. In other embodiments, the cerumen is softened by other means, such as by a doctor syringing the ear, and the current invention mechanically collects the softened cerumen.

It should be pointed out that, while the cerumen softening fluids are low viscosity softening fluids, the outgoing softened cerumen, which could be in the form of a liquid, a paste or a wax, and which has high viscosity since it is a cerumen/softening fluid mixture.

The core concept behind the present invention is to provide a simple mechanical device for cerumen removal.

According to some embodiments, the device described hereinafter is useable without the need for a physician to present.

According to other embodiments, the device is intended for the use of physicians such as general practitioners or ENT doctors. In these embodiments, the cerumen is softened by the doctor or other clinician using conventional techniques such as syringing or otherwise inserting into the ear canal a cerumen softening liquid, preferably (but not limited to) hydrogen peroxide. After the cerumen has softened, the doctor or other clinician will employ the device of the present invention to remove from the ear canal the softened cerumen. It is another core concept of the invention that the softened cerumen is amassed in the device and is removed, with the device, from the ear canal.

Figures 2A, 2B, 2C:
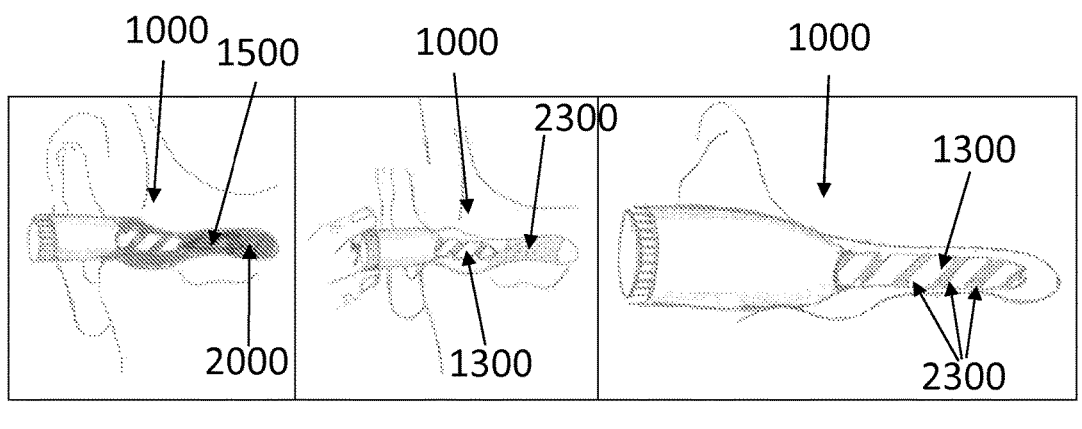
FIG. 2 schematically illustrates a device for removing cerumen from the ear.

FIGS. 2A-C describe an operational concept of the invention, rather than its final design. The liquid remains within the ear canal while being in contact with the cerumen for a certain amount of time. Optionally, the liquid may contain medications in the form of liquid, gel, or powder that are sometimes required for topical treatment such as external otitis or mycosis. Therefore, the current invention suggests a cerumen removal treatment using three sequential steps:

1. First step (FIG. 2A)—Cerumen immersion. With the device (1000) in the ear canal, fluid (1500) exits the device and wets the cerumen (2000).

It should be noted that in some variants of the device, the softening fluid is introduced into the ear in any manner known in the art, e.g. via a syringe, before insertion of the device into the ear.

Since hydrogen peroxide is a good cerumen softener and is often used in wax softeners, in preferred embodiments it is used as the softening agent. In other embodiments, the softening agent can be (but is not limited to) baby oil, glycerin, mineral oil, glycerol, olive oil, almond oil, docusate sodium (dioctyl sodium sulphosuccinate), dichlorobenzene, and carbamide peroxide, Hydrogen peroxide, solution of sodium bicarbonate, commercial earwax removal liquid, and any combination thereof.

2. Second step (FIG. 2B)—Cerumen collection. A collection mechanism, the collector head (1300) is introduced into the ear canal, in order to mechanically collect cerumen. Once the cerumen is soft (2300), the collector head (1300) of the device (1000) collects the softened cerumen (2300).

3. Third step (FIG. 2C)—Cerumen extraction. After the cerumen has been collected in the collector head (1300) of the device (1000), the device (1000), including the collector head (1300) and the softened cerumen (2300) held by it is removed from the ear canal.

The invention provides a single use, disposable product, designed, in some embodiments, for self-treatment by a patient at home. It can also be used, for non-limiting example, by a clinician or other caregiver treating a patient, in a clinical or residential setting. Non-limiting examples of treatment in a residential setting include a person treating himself or a parent treating a child. Other non-limiting examples include care of the physically frail (such as the elderly) or the physically or mentally disabled. Such care can be provided by the patient's family, by a caregiver, or by a physician. A non-limiting example of treatment in a clinical setting is use of the product by a doctor in the office as part of treatment.

In preferred embodiments, the overall process takes less than 5 minutes; in most embodiments, it takes less than 20 minutes.

The operation is quite simple; the device is inserted into the ear canal and rotational force is applied to a knob, the knob remaining on the exterior of the ear. The device is designed such that, when used properly, the user can not apply sufficient force in a longitudinal direction, inward along the ear canal, to force the cerumen inward. Furthermore, the device is designed such that, when used properly, the user exerts a substantially rotational force to the knob, e.g. by rotating it at a constant speed.

Safety considerations: the maximal travel of the cerumen collecting mechanism is about 0.5-1.5 cm so that the maximal ear canal penetration is 1.5-2.5 cm from the external ear, leaving a safety distance of a minimum of 0.5-1 cm from the tympanic membrane. Furthermore, only moment forces can be exerted by the user, as opposed to forces that might push the device towards the tympanic membrane thus significantly reducing the risk of tearing the membrane.

FIG. 3 illustrates the concept mechanism and its general action. The entire process is managed through an applicator (1000) that has several components:

1. A static mechanism (1100), referred to hereinbelow as the "device body", that is lodged in the external ear canal and which, in preferred embodiments, comprises a reservoir filled with about 1-5 ml of liquid. In preferred embodiments, the liquid is hydrogen peroxide 3%. Other possible liquids include, but are not limited to, other concentrations of hydrogen peroxide, oils such as mineral oil, baby oil or medicinal olive oil, sodium bicarbonate ear drops, and commercial ear drops such as, but not limited to, Earex™.

In some embodiments, the device does not comprise a reservoir of softening liquid. In such embodiments, the softening liquid is inserted into the ear by a physician or other clinician, in any manner known in the art, such as, but not limited to syringing. After insertion of the liquid and the passage of sufficient time for the liquid to soften the cerumen, the physician or other clinician inserts the device into the ear and operates it, thereby gently and reliably removing the softened cerumen from the ear.

In some embodiments, the reservoir of liquid is not within the main body of the device, but is within a container fluidly connected to the device and situated above the ear canal, for non-limiting example, at eye height, or resting above the ear between the upper portion of the pinna and the head, or on top of the head. In some of these embodiments, the reservoir can be held to the head by a ribbon tied around the head or by an elastic band, or by any other means known in the art of holding objects in place on the head. In embodiments where the reservoir is above the ear canal, liquid flow into the ear canal is aided by the force of gravity.

2. A dynamic mechanism (1200), referred to hereinbelow as the "knob", that uses the rotational forces exerted by the user for powering the device throughout the treatment.

A mechanism (not shown) that wets the cerumen's (2000) front, comprising a reservoir of softening liquid (not shown), an orifice (1400) to deliver the liquid to the ear canal and a fluid connection (not shown) between the reservoir (not shown) in the device body (1000) and the orifice (1400).

3. A mechanism (1300) that collects the cerumen (2000).

The applicator operates in the following manner: The applicator (1000) is inserted into the opening of the ear canal and the distal end (1500) of the static mechanism (1100) is lodged in the outer part of the ear. The user turns the knob (1200). This has two effects. The first is that the cerumen's front is wetted via the wetting mechanism (not shown) with a softening fluid such as, but not limited to, hydrogen peroxide. The wetting liquid is preferably delivered to the ear canal via the cerumen collector (1300) via at least one opening (1400) in the cerumen collector (1300). The second effect is that the knob (1200) imposes rotational maneuvers (curved arrow) that advance the collector (1300) in the direction (straight arrow) of the cerumen (2000). When the cerumen (2000) is soft, the collector head (1300) collects the soaked cerumen paste at the interface between the device and the hard cerumen. The tip of the cerumen collector (1300) does not progress into the ear canal if the cerumen is not soft enough. If the cerumen is too hard to be collected, the cerumen collector (1300) can collapse, it can rotate in place, or any other means known in the art can be used to prevent forward motion of the part of a collector head (1300) in contact with hard cerumen.

The distal end of the static mechanism, the nosepiece (1500), can be shaped like an earplug. Non-limiting examples of earplug shapes are shown in FIG. 3B to D. The distal end of the earplugs, the end which extends furthest into the ear canal, is to the right in FIGS. 3B to 3D.

The Knob (1200)

The knob comprises a dynamic mechanism (not shown) that uses the rotational forces exerted by the user to power the device during treatment. In some embodiments, a wire or cable (1110) is connected to the static mechanism (1100), the wire or cable transmitting the rotational motion of the knob to the collector in order to mechanically clean the ear canal. The device constrains the user so that the only allowed maneuvers are those that impose rotational forces rather than compression forces so as to prevent the possibility of injury in the region of the tympanic membrane. The rotational force is used to both direct the collector into the inner part of the ear canal while rotating (i.e. a screw motion) as well as to transfer liquids to the cerumen's front through the orifice (1400, not shown). It is possible, that the liquid will be transferred using another instrument such as a piston/syringe device. It is possible, as a safety measure, that an element that prevents pushing the cerumen is added such that, when cerumen blocks the way or is still hard, the collector will remains in its position rather than be pushed in the direction of the tympanic membrane so as not to impose an unnecessary risk such as tearing the membrane.

In preferred embodiments, the knob mechanism comprises a clutch or other decoupling mechanism such that, after the collector head has been extruded by a predetermined distance, preferably no more than 1 cm, further rotation of the knob produces no further extrusion of the collector head.

Collector Head (1300)

The cerumen collector head (1300) "digs" the cerumen and collects it, but cannot push cerumen. The reason it cannot push cerumen into the ear canal is because it is designed to collapse under a predetermined pressure which is less than the pressure required to push cerumen; the collector head (1300) has low longitudinal rigidity.

Furthermore, the collector head (1300) is designed to have low resistance to bending so as to facilitate its insertion into the inner part of the ear canal (note that the ear canal is tortuous in all three dimensions).

Embodiments for a mechanism for the collector head (1300) include, but are not limited to, a collector head comprised of soft material and shaped like a milling bit or Archimedes screw (diameter about 4-5 mm, length about 10 mm); a thin-walled hollow pipe with the ability to vary at least a portion of its cross sectional diameter to fit the diameter of the ear canal and the ability to vary the direction of portions of its longitudinal axis to follow the sigmoid shape of the ear canal; a thin-walled hollow pipe design having inner protrusions; a braided basket design; a sponge design, a scoop design and a shovel design. Other embodiments will be obvious to persons skilled in the art.

In embodiments with integral reservoir of cerumen-softening liquid, the reservoir can be within the collector, within the device body (static mechanism), and any combination thereof. In other embodiments comprising a reservoir, the reservoir can be fluidly connected to the device body, and be emplaced above the level of the device body (and the ear canal), such as on top of the ear between the pinna and the head, or at eye level or on top of the head. In the last two embodiments, the reservoir can be held in position by a ribbon or by an elastic band, or by any other means known in the art of holding objects in place on the head.

Figure 4:
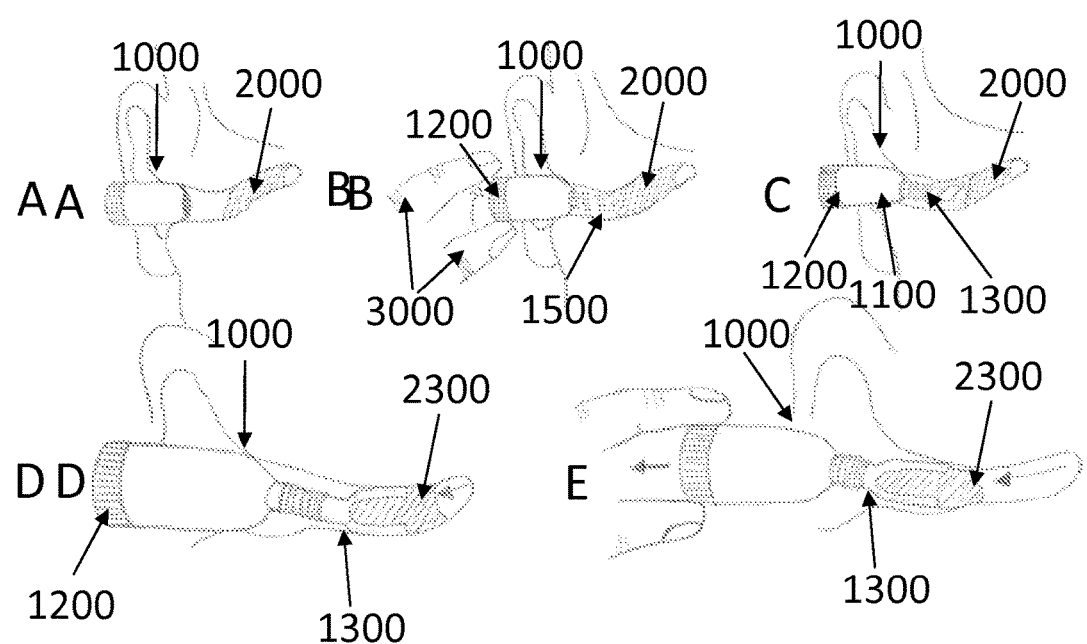
FIG. 4 schematically illustrates a process of using a device for removing cerumen from the ear.

In an exemplary embodiment of the concept (FIG. 4A-F), a procedure for using the device is shown. In the first step (FIG. 4A), the device (1000) is inserted into the outer part of an ear canal contained impacted cerumen (2000).

In the second step (FIG. 4B), the knob (1200) of the device (1000) is turned (arrow) by a hand (3000). This induces flow of cerumen-softening liquid (1500) into the ear canal, where it contacts the cerumen (2000) and softens it.

In the third step (FIG. 4C), further rotation of the knob (1200) extrudes the collector head (1300) from the device body (1100), causing it to contact the cerumen (2000), which is now at least partly softened.

In the fourth step (FIG. 4D), the user continues to rotate the knob (1200), so that the collector head (1300) extends further from the device body (1100), thereby collecting the softened cerumen (2300).

The wetting process can be intermittent or continuous. In some embodiments, intended primarily for use by physicians or other clinicians, the cerumen is wetted and softened by the softening liquid separately, for example, by a syringe, before the device is inserted in the ear. In such embodiments, the device does not comprise a reservoir and operating the device comprises collecting the softened cerumen and removing it from the ear canal.

In other embodiments, at the start of the process, all of the softening liquid is dispensed into the ear, after which the softened cerumen is collected and removed from the ear canal.

In yet other embodiments, the softening liquid is dispensed continuously, simultaneously with collection of the softened cerumen. In these embodiments, it is preferred that the dispensing of softening liquid begins before collection starts, so that, by the time the collector head reaches the cerumen, the cerumen has been softened and is collectable.

In still other embodiments, release of the softening liquid and operation of the collector are both intermittent. In these embodiments, softening liquid is released, after which the collector head collects the softened cerumen. Then further softening liquid is released, followed by collection of the softened cerumen. The steps of releasing softening liquid and collecting cerumen can be repeated a plurality of times. As a non-limiting example, (a) the softening liquid is dispensed for 2 rotations of the knob, followed by (b) 2 rotations of the knob during which there is neither dispensing of liquid nor rotation of the collector head. This is followed by (c) 10 rotations of the knob during which the collector head collects softened cerumen. The process (a), (b), and (c) is repeated 20 times, for a total of 280 rotations of the knob. The device is then removed from the ear canal.

In the last step (FIG. 4E), the device (1000) is removed from the ear canal (arrow), with the softened cerumen (2300) being thereby removed from the ear canal, since it is held by the collector head (1300).

In some variants, the collector head (1300) is retracted into the device body (1100) during the removal step, in other embodiments (shown), the collector head (1300) is partially retracted into the device body (1100), in yet other variants, the collector head (1300) remains extended during removal of the device (1000) and the softened cerumen (2300) from the ear canal.

Any mechanism known in the art can be used to retract the collector head into the device body. Typical mechanisms include, but are not limited to, a wire or cable attached at one end to the collector head or to some portion of the distal end of the shaft, wherein, if a portion of the wire or cable is pulled, the collector head is withdrawn into the device body; a collapsible or telescopic shaft that, when collapsed, pulls the collector head into the device body, a rotatable shaft that, when rotated, screws the collector head into the body, a direct coupling, e.g., to the knob or to a second knob, that, when the knob is rotated, the collector head retracts into the body, or any combination thereof.

FIG. 5A-D shows the effects of cerumen softening liquid on a plug of hardened cerumen.

Figure 5:
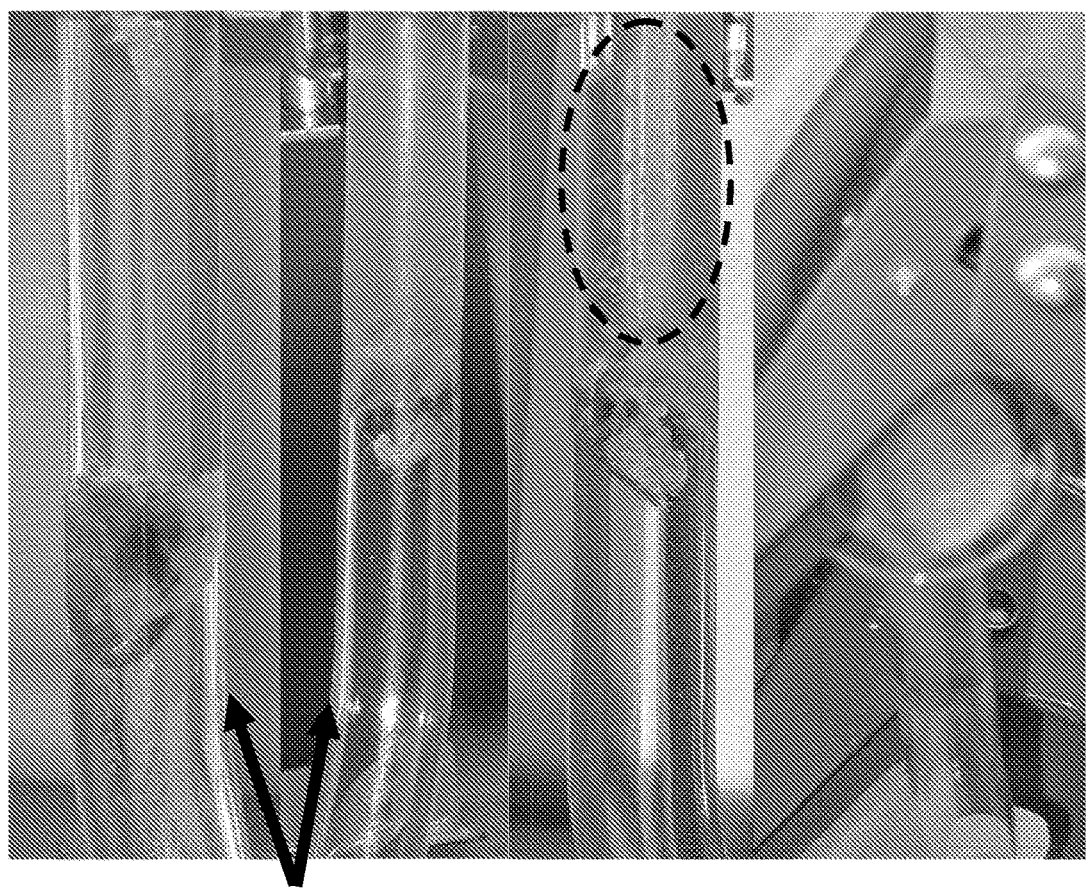
FIG. 5 depicts the softening of cerumen exposed to a cerumen softening liquid.

In FIG. 5A, the plug of hardened cerumen is shown. It is a hard mass with a density is such that it floats in the liquid close to the bottom of the tube (slightly above the bend in the tube, arrow).

In FIG. 5B, the cerumen has absorbed some of the softening liquid; its density has decreased so that part of it floats higher up in the liquid. Its volume has also increased and it has become softer.

In FIG. 5C, the softening process continues; small fragments of the cerumen are detaching from the plug and are drifting to the top of the tube (circle).

In FIG. 5D, the process is complete; the cerumen is now a soft paste with some cerumen particles floating at the top of the liquid (dotted arrow).

In some embodiments, the device is inserted into the ear canal manually. In other embodiments, the device comprises an insertion mechanism whereby, when the device is placed against the external ear, it is automatically inserted therein.

In some embodiments, at least a portion of the device body comprises a biodegradable shell. In such embodiments, the device is placed in the ear canal and left there. The shell biodegrades and, after a predetermined time, it ceases to restrict the movement of the collector head, which is extended into the ear canal by a spring-like device in the device body.

The biodegradable shell can be comprised of biodegradable polythene, beeswax, biodegradable polyethylene, biodegradable polypropylene, Poly-L-Lactides (polylactic acid, plla), Polyglycolide (polyglycolic acid, pga), Poly Lactic-co-Glycolic Acid (PLGA) any other material that degrades within less than an hour when in contact with an ear canal, and any combination thereof.

Devices with an automatic insertion mechanism and devices which operate automatically (such as, but not limited to, the device with biodegradable shell) are especially useful in the care of persons who, due to physical or mental infirmity, have difficulty inserting the device or for whom it is difficult for a physician or caregiver to insert the device.

Examples of embodiments of collector head designs are disclosed hereinbelow.

Example 1

FIG. 6 illustrates an embodiment of the collector head in the form of an Archimedes screw with soft blades (1300). In this embodiment, the Archimedes screw is rotated by a rotational force applied to the collector head (1300) via the knob (1200) by the user. The blade tips (1312) remove the softened cerumen from the impacted mass; the removed cerumen then travels along the blades toward the outside of the ear canal. Note that the blades' soft and narrow design allows bending and thus the collector head fits the dimension of the ear canal at different depths of the canal (note that the ear canal is not homogenous in its diameter along its length, and also differs between different users).

FIG. 6A illustrates the Archimedes screw design with the screw (1310) at its innermost position (within the device body).

FIG. 6B illustrates the Archimedes screw design with the screw (1310) at an outer position, showing the screw (1310) and the blade tips (1312).

FIG. 6C illustrates the Archimedes screw design partially disassembled, with the knob (1200) removed, showing the extruding mechanism (1314) for the Archimedes screw and the device body (1100). A clutch like mechanism (1316) disconnects the motion between knob (1200) and the extruding mechanism (1314) when the extruding mechanism is displaced about 1 cm. The extruding mechanism (1314) is connected to the Archimedes screw (1310) so that its disconnection is required so as prevent it from advancing further in the direction of tympanic membrane, although the user may continue to turn the knob (1200). The clutch mechanism ensures that, although the Archimedes screw continues to turn, it cannot advance further.

FIG. 6D illustrates an exploded view of the Archimedes screw design. The exploded view shows the knob (1200), the extruding mechanism (1314) for the Archimedes screw (1310), the outer housing (1100) for the device, the clutch like mechanism (1316), and the nosepiece (1500) which fits into the outer ear and from which the Archimedes screw (1310) will protrude.

Figure 6E:
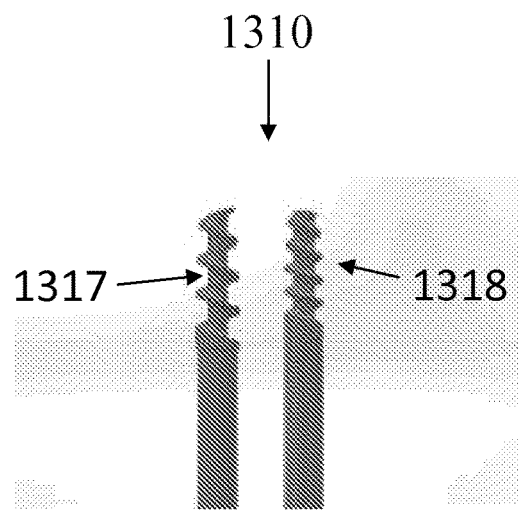
FIG. 6 schematically illustrates an embodiment of the device.

FIG. 6E illustrates two different Archimedes screw (1310) designs. The left Archimedes screw (1317) has a coarse pitch, while the right Archimedes screw (1318) has a fine pitch.

The Archimedes screw (1310) can be composed of soft materials such as, for non-limiting example, silicone, fiber mesh, cellulose, polyurethane, polyethylene, polyamide, polypropylene, and any combination thereof.

The Archimedes screw (1310) can comprise a single piece, or it can comprise a plurality of segments connected by a flexible section, said flexible section comprising accordion pleating, a spiral spring or a hinging means, the flexible section allowing the Archimedes screw (1310) to deform to follow the tortuosity of the ear canal. The hinging means can comprise a hinging mechanism, or it can comprise a shaft comprising a plurality of hinging sections, as described hereinbelow.

The flexible section, by enabling bending in all three dimensions, prevents resistance of the collector head to bending, especially about its longitudinal axis and ensures that the Archimedes screw conforms to the tortuosity of the ear canal.

Example 2

Figure 7:
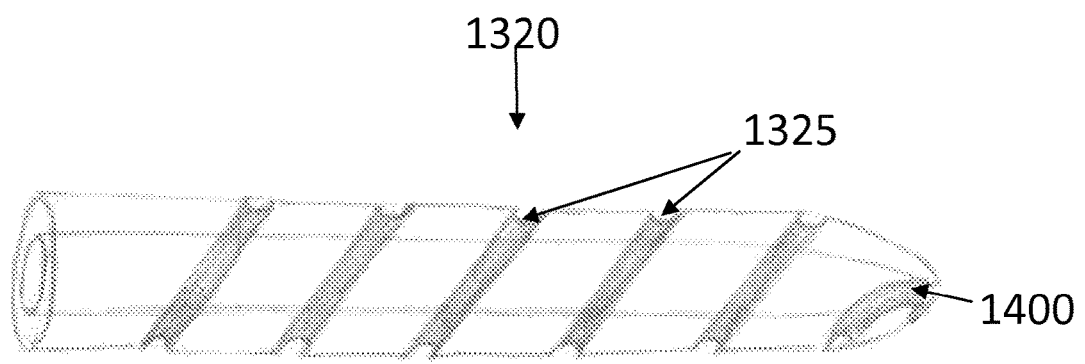

FIG. 7 discloses an embodiment of the collector head in the form of a milling bit (1320) composed of soft materials, for non-limiting example, silicone, fiber mesh, etc. In the bit design, cerumen is wetted by fluid supplied from a reservoir (not shown) through an inner pipe (not shown) and orifice (1400). Cerumen is collected within the bit's grooves (1325) as the bit is rotated within the ear canal.

The milling bit (1320) can be composed of soft materials such as, for non-limiting example, silicone, fiber mesh, cellulose, polyurethane, polyethylene, polyamide, polypropylene, and any combination thereof.

The milling bit (1320) can comprise a single piece, or it can comprise a plurality of segments connected by a flexible section, said flexible section comprising accordion pleating, a spiral spring or a hinging means, the flexible section allowing the milling bit (1320) to deform to follow the tortuosity of the ear canal. The hinging means can comprise a hinging mechanism, or it can comprise a shaft comprising a plurality of hinging sections, as described hereinbelow.

The flexible section, by enabling bending in all three dimensions, prevents resistance of the collector head to bending, especially about its longitudinal axis and ensures that the milling bit conforms to the tortuosity of the ear canal.

Example 3

FIG. 8 discloses an embodiment of the collector head formed as a plurality of fibers braided into a form which, when fully extended, resembles a basket. This embodiment will be referred to hereinafter as the "braided basket" (1340). In the braided basket design, the braiding forms a hollow, preferably closed-ended pipe composed of elastic fibers. The braiding facilitates the expansion of the braided basket to match the dimensions of the ear canal at any location within the ear canal. With this design, the basket (1346) is in its minimal diameter mode when it is retracted and at least substantially inside a sleeve (1343) and it opens to an expanded position when extended at least partly outside the sleeve (1343). In its open state, the basket (1346) captures the cerumen and, when the sleeve (1343) covers the basket (1346) entirely or partially, it reduces the diameter of the basket (1346) and thereby collects the cerumen within the bore of the braided basket (1346).

In use, the device is inserted into the ear canal with the braided basket (1346) in its retracted position. The knob is rotated, which extends the braided basket (1346) from the sleeve (1343) and rotates the braided basket (1346). Rotation of the braided basket (1346) collects the softened cerumen within the basket. When the device is to be removed from the ear canal, the braided basket (1346) is retracted into the sleeve (1343), thereby trapping the cerumen inside the collector head (1340) and ensuring its removal from the ear canal.

The fibers comprising the basket can be of any sufficiently stiff, sufficiently elastic material. Fiber materials include, but are not limited to, steel, nickel-titanium, beta-titanium, plastic and any combination thereof. The material can be monofilament i.e., comprising a single fiber, or multifilament, comprising a plurality of fibers.

Multifilament fibers can comprise filaments wound around each other without a core, filaments wound around a core, filaments braided together, and any combination thereof. The filaments can be identical or can differ. For example, the core can comprise a filaments thicker or of a stiffer material than the wrapping filaments.

The fibers can be coated. Each filament of a multifilament fiber can be individually coated, or the fiber itself can be coated.

Coatings can improve, among other factors, stiffness, breaking strength, flexibility, slidability of the fibers against each other (non-stick coatings), and biocompatibility.

Fiber materials can include, but are not limited to, metal, plastic, natural fibers, polyester, rayon, nylon, woven material, non-woven material and any combination thereof.

Fiber coatings can include, but are not limited to, metal, plastic, Teflon, natural fibers, polyester, rayon, nylon, woven material, non-woven material and any combination thereof.

FIG. 8A shows an embodiment of a braided basket design in a retracted position. Part of the braided basket (1346) is visible at the end of the sleeve (1343).

FIG. 8B shows an embodiment of the braided basket design when slightly extended. The braided basket (1346) is clearly visible at the end of the sleeve (1343) and has expanded so that it is significantly wider than the sleeve (1343).

FIG. 8C shows an embodiment of the braided basket design when significantly extended. The braided basket (1346) is wider than when slightly extended and extends further from the end of the sleeve (1343).

FIG. 8D shows an embodiment of the braided basket design when in a fully extended state. The shaft (1343) holding the braided basket (1346) can be clearly seen, and the braided basket (1346) is now basket-shaped rather than the more conical shape seen in FIGS. 8A-8C.

It is clear that fluid can easily pass from the hollow sleeve and through the braiding of the basket to reach the cerumen.

Example 4

Figure 9A:
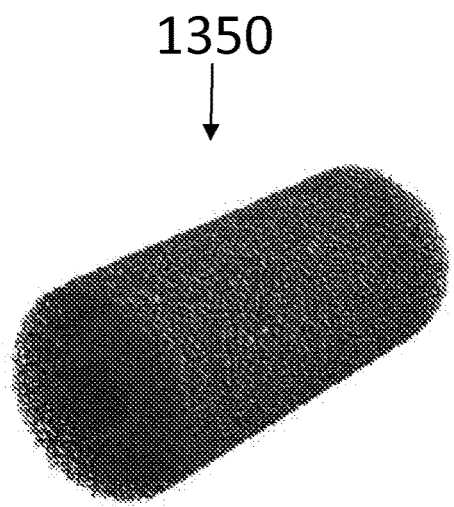

FIG. 9A illustrates an embodiment of the collector head formed of a sponge (1350). In this design, the collector head is of a substantially cylindrical shape and is formed of a spongy material. The sponge is kept wet by the fluid from the reservoir; the fluid flows through the sponge and wets portions of the cerumen's front. Rotation of the sponge causes collection of the softened cerumen within the pores of the sponge. The sponge is elastic so that it can deform to fit the size and shape of the external ear canal.

The sponge can be formed in other shapes such as, but not limited to, a cone or the frustum of a cone.

The sponge can be mounted directly to the knob or can be connected to the knob via a shaft or sleeve or other connecting mechanisms as is known in the art. One embodiment of such a shaft is described hereinbelow.

The sponge can be comprised of materials including, but not limited to, cellulose, polyurethane, polyamide, Polypropylene, polyethylene, and any combination thereof.

Figure 9B:
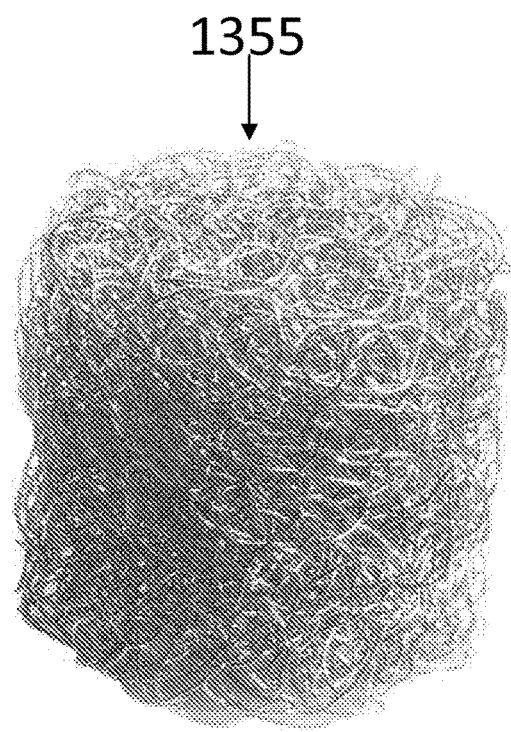

FIG. 9B illustrates another embodiment (1355), in which the sponge is composed of fine fiber twisted, crumpled, bent or braided so as to form a body composed of fiber. The exemplary embodiment of FIG. 9B is formed of fiber bent into the form of a cylinder; the fiber body can be formed in other shapes such as, but not limited to, a cone or the frustum of a cone.

It should be pointed out that, while the cerumen softening fluids are low viscosity softening fluids, the outgoing soft cerumen, which could be in the form of a liquid, a paste or a wax, has high viscosity since it is a cerumen/softening fluid mixture.

Example 5

FIG. 10 illustrates a method of using a collector head in the form of a hollow pipe (1360). With the hollow pipe design, as the leading (distal) edge of the pipe advances inward toward the eardrum, a new front of cerumen (2000) is wetted and is collected by the cerumen collector. This process is repeated constantly until the ear canal is cleared.

The hollow pipe is composed of a very thin elastic foil. The elastic foil is folded around and is made of sufficiently elastic spring-like material so that it has radial elastic forces (like a watch spring) towards the ear canal walls in order to increase or reduce its diameter according to its location within a tunnel such as the ear canal. The rationale is that the elastic foil is spring-like enough that it is pressed against the walls of the ear canal. This, along with the thinness of the foil, ensures that the elastic foil collector head passes between the cerumen in the ear canal and the walls of the ear canal, so that the cerumen is surrounded by the foil collector head and collected within it. Furthermore, the radial forces ensuring that the elastic foil is pressed against the walls of the ear canal prevent the foil collector head from pushing the cerumen deeper into the ear canal.

Figure 10A:
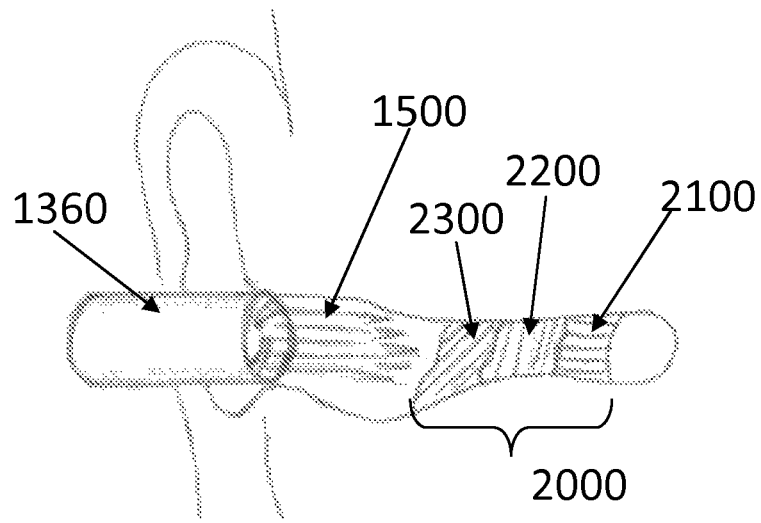
Figure 10B:
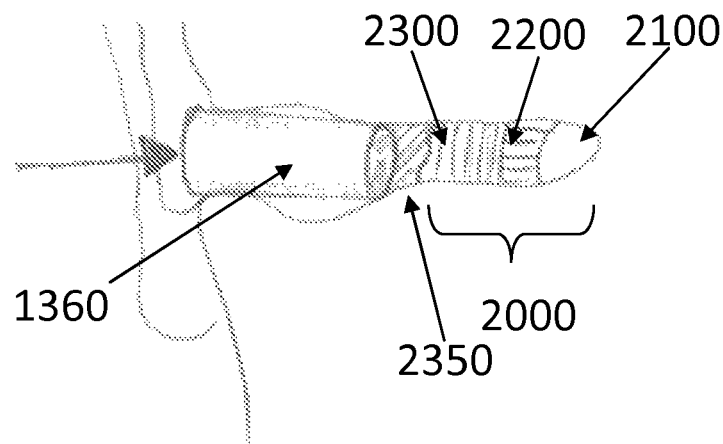
Figure 10C:
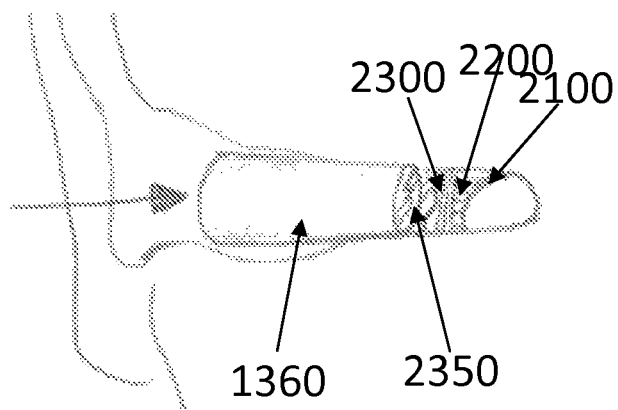

FIGS. 10A-C show the functioning of the hollow pipe design. Liquid (1500) exiting the pipe (1360) wets the cerumen (2000) and softens it, producing fully wetted cerumen (2300) and, further from the pipe opening, partially wetted cerumen (2200), while unwetted cerumen (2100) remains in the regions furthest from the pipe.

FIG. 10A illustrates the situation at the start of the process. At this point, the pipe (1360) has not reached the cerumen (2000), although the wetting fluid (1500) has, producing partly wetted cerumen (2200) and fully wetted cerumen (2300), although some of the cerumen (2100) is still unwetted.

FIG. 10B illustrates the situation after the pipe (1360), moving inward (arrow), has reached the cerumen (2000). Some of the fully-wetted cerumen has been collected inside the pipe (2350) and the wetting fluid (not shown) is softening additional portions of the cerumen plug (2200). The amount of unwetted cerumen (2100) has decreased.

As the process continues (FIG. 10C), the pipe (1360) continues to move inward toward the base of the external ear canal (arrow) and to collect the wetted cerumen within it (2350). Near the end of the process, as shown in FIG. 10C, most of the wetted cerumen (2300) has been collected; only small amounts of partially wetted (2200) and unwetted cerumen (2100) remain.

FIG. 11 illustrates another embodiment of a hollow pipe design, comprised of a very thin (in the range of 0.05 mm thick to 0.5 mm thick, preferably approximately 0.1 mm thick) elastic foil. The elastic foil is made of a spring-like material and is folded around so there exist in it radial elastic forces which enable it to increase or decrease its diameter in order to conform to the shape of the walls of the ear canal. The rationale is that the elastic foil is spring-like enough that the elastic foil is pressed against the walls of the ear canal. This, along with the thinness of the foil, ensures that the elastic foil collector head passes between the cerumen in the ear canal and the walls of the ear canal, so that the cerumen is surrounded by the foil collector head and collected within it. Furthermore, the radial forces ensuring that the elastic foil is pressed against the walls of the ear canal prevent the foil collector head from pushing the cerumen deeper into the ear canal.

Because the diameters of collector leading (distal) edge, ear canal and cerumen plug are approximately the same, the collector can encompass the cerumen and because of the thinness of the material of the thin hollow pipe, the collector can advance between the cerumen and the wall of the ear canal. As the collector advances, its diameter and especially the diameter of its leading portion reduces, since the diameter of the ear canal is decreasing.

At some point, some portion of the leading (distal) portion of the collector will undergo plastic deformation. Having undergone plastic deformation, the leading (distal) portion of the collector will remain in approximately its final, deformed shape and will not regain its original expanded shape upon removal from the ear, thereby ensuring retention of the cerumen within the collector.

In preferred embodiments, the elastic foil material does not undergo plastic deformation. In these embodiments, the collector comprises a ring, preferably a metal ring (hereinafter referred to as the 'deformable ring'), approximately at the collector's leading (distal) edge, which undergoes the appropriate plastic deformation when the foil collector head is approximately at its furthest depth within the ear canal.

In preferred embodiments, the collector, at the end of treatment, has been reshaped into a substantially conical shape and, therefore, a substantially closed-sided and closed-ended shape so that, when the device is removed from the ear, the collector retains the captured cerumen.

Since the cerumen is efficiently collected within the foil, removal of the device from the ear also removes the cerumen therefrom. The plastic deformation of the deformable ring by the ear canal, by tending to close the opening at the distal end of the foil collector head, increases the efficiency of removal of the cerumen from the ear.

In some embodiments, the foil collector head further comprises a deformable ring at its proximal end; in these embodiments, the foil collector head comprises deformable rings at both the distal and the proximal ends.

The pipe can be composed of any material capable of forming a very thin, highly elastic foil. In some embodiments, the foil is comprised of polyimide. Other foil materials comprise polyvinyl chloride (PVC), PEEK, PE, PP, Polyamid and laminates of thermoplastic elastomers and thermoplastic plastics. Any material capable of forming a very thin, highly elastic, foil (between 0.05 mm thick and 0.5 mm thick, preferably approximately 0.1 mm thick) known in the art can be used. The foil can, optionally, also be stiffened with struts or other stiffening mechanisms known in the art.

Figure 11A:
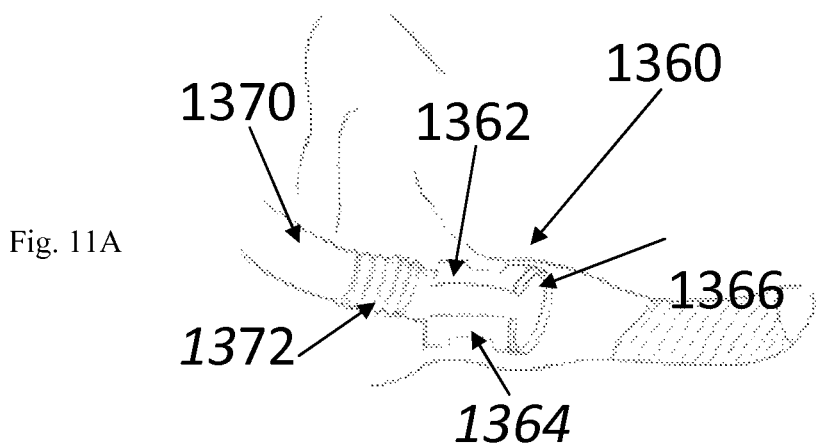
Figure 11B:
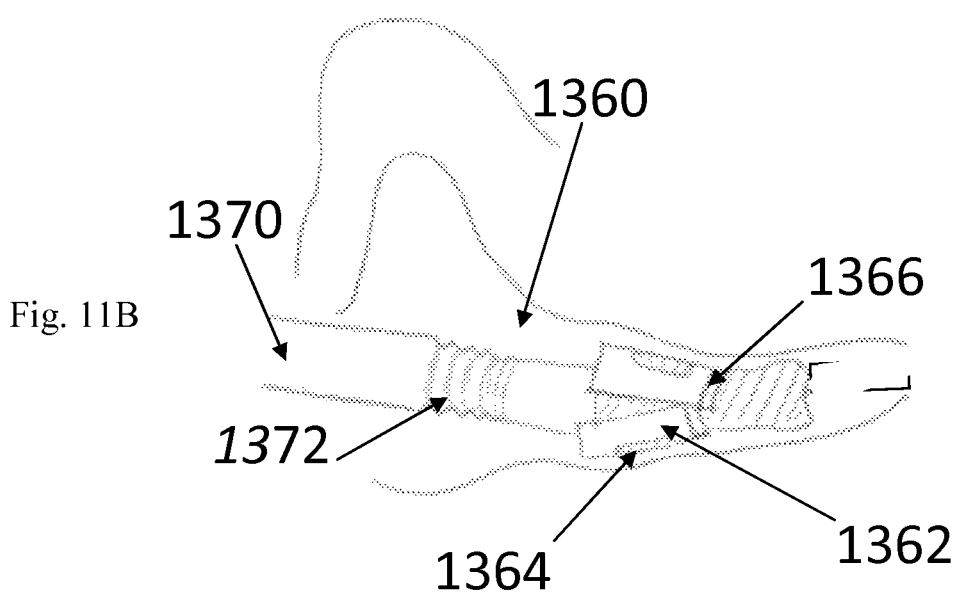

FIG. 11A illustrates a perspective view of an embodiment of the thin hollow pipe collector (1360), while FIG. 11B illustrates a side view of the collector (1360). The collector (1362) is attached to a, preferably, flexible shaft (1370) with a flexible section (1372). In this embodiment, the elastic foil (1362) comprises gaps (1364) adapted to fine-tune the flexibility of the foil By using gaps of different sizes and/or shapes, the same thickness of foil can be used for ear canals of different sizes, for non-limiting example, for adults and for children.

The flexible section, by enabling bending in all three dimensions, prevents resistance of the shaft to bending, especially about its longitudinal axis, and ensures that the longitudinal axis of the foil distal end conforms to the tortuosity of the ear canal.

In the embodiment shown in FIG. 11, the flexible section (1372) comprises accordion pleating. The flexible section (1372) in the shaft, by enabling bending in all three dimensions, increases the flexibility of the collector head while within the ear canal, prevents resistance of the shaft to bending, especially about its longitudinal axis, and directs the head towards the cerumen, by providing sufficient flexibility to the shaft in all three dimensions that the foil is in the same orientation as the cerumen.

The accordion pleating can be in the form of a plurality of substantially straight, substantially parallel rows, or it can be in the form of a continuous spiral, or any combination thereof, so that the accordion pleating allows the shaft to bend in all three dimensions.

In other embodiments (described hereinbelow), the flexible section can comprise a spiral spring, a more flexible material, a plurality of thin regions hingedly connecting stiffer regions, a plurality of regions comprised of a more flexible material hingedly connecting stiffer regions, and any combination thereof.

Figure 11C:
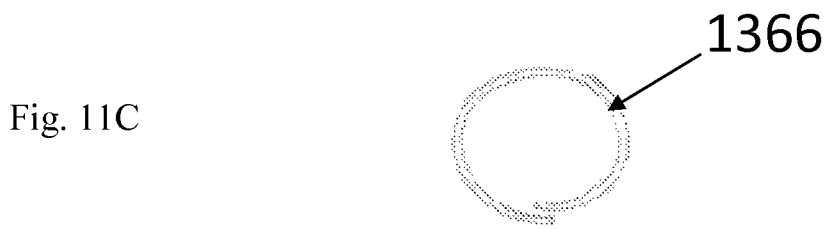

FIG. 11C illustrates a front view of the deformable ring in its compressed state (1366).

In FIGS. 11A and B, the thin foil (1362) comprises substantially the frustum of a cone, open at one edge to allow the cone to easily change its diameter and cone angle to match those of the ear canal, where the narrow end of the cone (at the right in FIGS. 11A and B) forms the leading (distal) edge and is deeper in the ear canal than the wide (proximal) end of the cone (at the left in FIGS. 11A and B).

In some embodiments, the elastic foil comprises, on its inner side, protrusions (not shown) adapted to collect the cerumen and guide the cerumen in the foil proximally, toward the shaft (1370), thereby clearing the distal portion of the elastic foil and allowing the elastic foil to collect further cerumen.

The height of the protrusions varies, starting from zero at their distal end and increasing towards their proximal end. In preferred embodiments, the height of the protrusions is a maximum near their proximal end, so that the protrusions collect the cerumen but do not push it, thereby preventing the device from forcing the cerumen deeper into the ear canal.

In preferred embodiments, the protrusions form at least the segment of a spiral, the spiral wrapping around the side of the frustum of the cone.

The protrusions can, in addition to guiding the cerumen, also function as struts to stiffen the elastic foil.

The leading (distal) edge (at the right in FIGS. 11A and B) can also comprise a deformable ring (1366) which will plastically deform if compressed sufficiently and, in use, will deform at approximately the point when the leading (distal) edge of the collector reaches its maximum depth in the ear canal.

Figure 12:
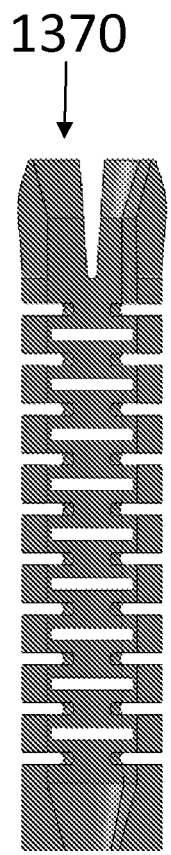
FIG. 12 schematically illustrates a shaft for a collector head.

FIG. 12 illustrates another embodiment of a shaft (1370) to hold the elastic foil collector head and direct it to the cerumen site. One of the main obstacles to inserting instruments into the ear canal is the tortuous shape of the canal and thus the high chance of injuring the ear canal wall during entry. In order to prevent pain and/or injury, the shaft is designed to bend in all three axes to follow the ear canal whenever it encounters a bend in any of the three dimensional directions.

Example 6

Figure 13:
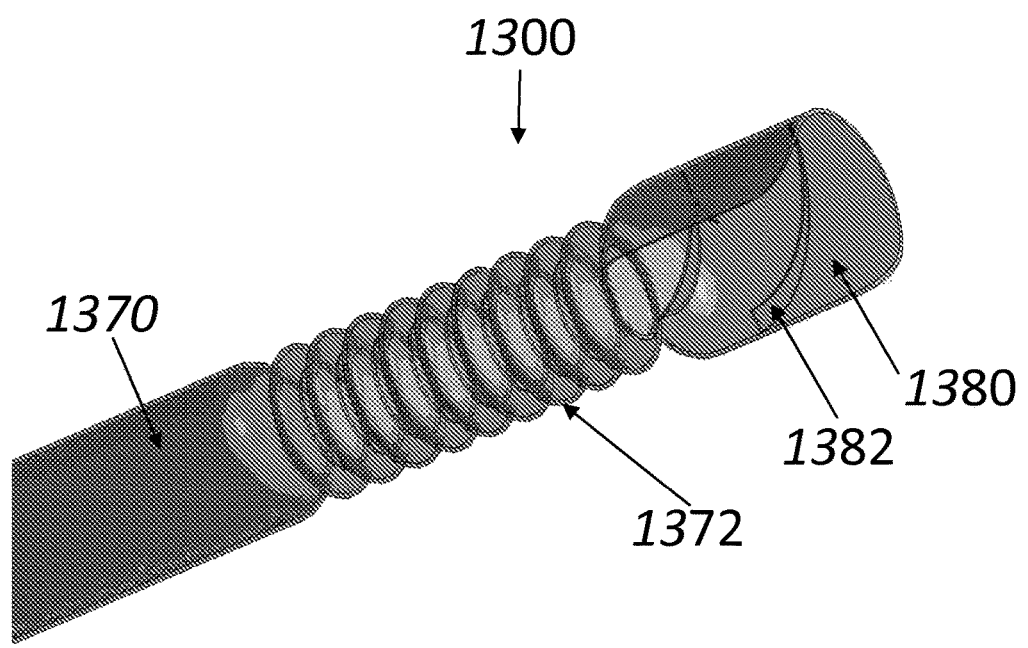
FIGS. 13-14 schematically illustrate embodiments of the collector head.

FIG. 13 illustrates an embodiment of a collector (1300) with a scoop head (1380). The embodiment comprises a, preferably, flexible shaft (1370), a flexible section (1372) comprising, in this embodiment, accordion pleating, to provide flexibility, and a collector head (1380) shaped substantially like a scoop with a transverse cross-section which forms a segment of a circle, in this embodiment, approximately a half-circle. As the collector rotates, the sides of the collector head (1380) will scrape at or near the wall of the ear canal, thereby collecting the cerumen within the scoop (1380).

The material of the scoop is of a spring-like elastic material, such that the scoop, especially the edges thereof, is gently pressed against the walls of the ear canal. This ensures that the scoop passes between the cerumen and the walls of the ear canal, facilitating collection of the cerumen and preventing the scoop from pushing the cerumen deeper into the ear canal.

The flexible section, by enabling bending in all three dimensions, prevents resistance of the collector head to bending, especially about its longitudinal axis and ensures that the collector conforms to the tortuosity of the ear canal along its entire length.

The accordion pleating can be in the form of a plurality of substantially straight, substantially parallel rows, it can be in the form of a continuous spiral, or any combination thereof, so that the accordion pleating allows the shaft to bend in all three dimensions.

In other embodiments (described hereinbelow, the flexible section can comprise a spiral spring, a more flexible material, a plurality of thin regions hingedly connecting stiffer regions, a plurality of regions comprised of a more flexible material hingedly connecting stiffer regions, and any combination thereof.

In preferred embodiments, the scoop head also comprises at least one vane (1382) to collect the cerumen and guide the cerumen in the scoop proximally, toward the shaft (1370), thereby clearing the distal portion of the scoop and allowing the scoop to collect further cerumen. The embodiment shown comprises two such vanes.

The height of the vanes varies, starting from zero at the vanes' distal end and increasing towards the vanes' proximal end. In preferred embodiments, the height of the vanes is a maximum near their proximal end, so that the vanes collect the cerumen but do not push it, thereby preventing the device from forcing the cerumen deeper into the ear canal.

In another variant of the scoop head collector, the means of guiding the cerumen to move proximally is at least one ridge. In all variants, the collection/guidance means varies in height from 0 at the distal end to a maximum near the proximal end.

The vanes or ridges preferably form segments of a spiral around the inside of the collector head. Spiral vanes or ridges can be arranged such that the distal ends of the spirals are separated longitudinally, as shown in FIG. 14, they can be separated transversely, for non-limiting example, such that two spirals both end at the distal end of the collector, and any combination thereof.

In some embodiments, the scoop has no vanes or ridges.

Example 7

Figure 14:
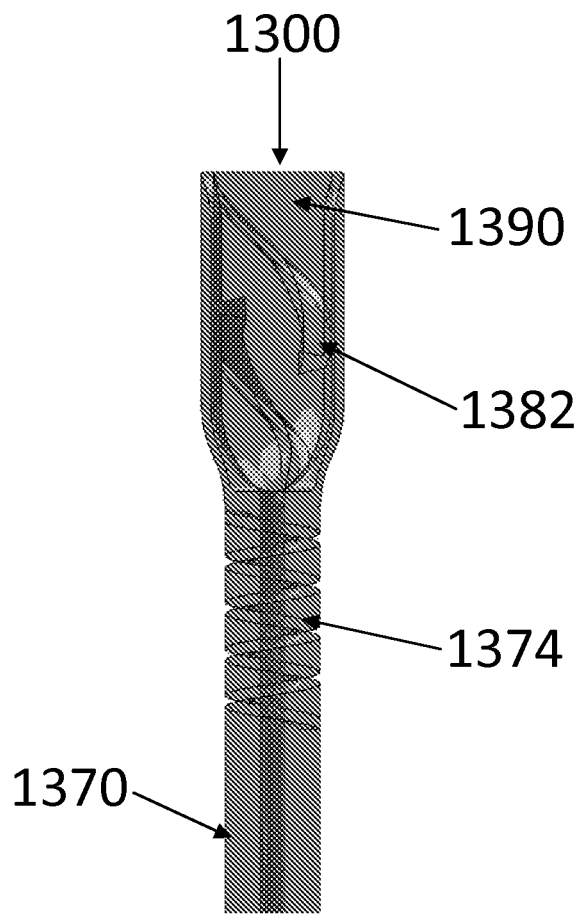

FIG. 14 illustrates an embodiment of a shovel collector (1300) with a shovel head (1390). The embodiment comprises a, preferably, flexible shaft (1370), a flexible section (1374) to provide flexibility and a collector head (1390) shaped substantially like a shovel, with a transverse cross-section which is substantially U-shaped, being slightly curved in its center, with curved, nearly vertical sides. As the collector rotates, the sides of the collector head (1390) will scrape at or near the wall of the ear canal, thereby collecting the cerumen within the shovel (1390).

The material of the shovel is of a spring-like elastic material, such that the shovel, especially the edges thereof, is gently pressed against the walls of the ear canal. This ensures that the shovel passes between the cerumen and the walls of the ear canal, facilitating collection of the cerumen and preventing the shovel from pushing the cerumen deeper into the ear canal.

The flexible section, by enabling bending in all three dimensions, prevents resistance of the collector head to bending, especially about its longitudinal axis and ensures that the collector conforms to the tortuosity of the ear canal along its entire length.

The flexible section can comprise accordion pleating, a spiral spring, a more flexible material, a plurality of thin regions hingedly connecting stiffer regions, a plurality of regions comprised of a more flexible material hingedly connecting stiffer regions, and any combination thereof.

The accordion pleating can be in the form of a plurality of substantially straight, substantially parallel rows, it can be in the form of a continuous spiral, or any combination thereof, so that the accordion pleating allows the shaft to bend in all three dimensions.

In preferred embodiments, the scoop head also comprises at least one vane (1382) to collect the cerumen and guide the cerumen in the shovel proximally, toward the shaft (1370), thereby clearing the distal portion of the shovel and allowing the shovel to collect further cerumen. The embodiment shown comprises two such vanes.

The height of the vanes varies, starting from zero at the vanes' distal end and increasing towards the vanes' proximal end. In preferred embodiments, the height of the vanes is a maximum near their proximal end, so that the vanes collect the cerumen but do not push it, thereby preventing the device from forcing the cerumen deeper into the ear canal.

In another variant of the shovel head collector, the means of guiding the cerumen to move proximally is at least one ridge.

In all variants, the collection/guidance means varies in height from 0 at the distal end to a maximum near the proximal end.

The vanes or ridges preferably form segments of a spiral around the inside of the collector head. Spiral vanes or ridges can be arranged such that the distal ends of the spirals are separated longitudinally, as shown in FIG. 14, they can be separated transversely, for non-limiting example, such that two spirals both end at the distal end of the collector, and any combination thereof.

In some embodiments, the shovel has no vanes or ridges.

In the embodiment shown, the flexible section (1374) comprises triangular segments connected by linear sections providing hinging between the triangular segments. In this embodiment, the hinging sections are thinner than the triangular segments they connect.

It is obvious that the flexible section can have accordion pleating (1372), can comprise a spiral spring, can be segmented and connected by hinging sections (1374), or any combination thereof. Other means of providing flexible connections, as is known in the art, may be used.

Preferred embodiments of collector heads designs such as the scoop or shovel or variants thereof Preferred shaft embodiments incorporate at least one flexible section, in addition to the flexibility comprised in the shaft by virtue of the flexible material of which it is comprised. Preferred embodiments of the shaft comprise a flexible section near the distal end of the shaft and, therefore, close to the collection portion of the collector head. The flexible section, by enabling bending in all three dimensions, both prevents resistance of the collector head (including the shaft, if present) to bending, especially about its longitudinal axis and enables the collection portion, the distal end of the collector head, to accurately conform to the orientation of the ear canal.

The flexible section can comprise accordion pleating, a spiral spring, a more flexible material, a plurality of thin regions hingedly connecting stiffer regions, a plurality of regions comprised of a more flexible material hingedly connecting stiffer regions, and any combination thereof. The main purpose of the flexible section is to allow the shaft to bend in all three dimensions so as to enable the collector head to follow the tortuosity of the ear canal.

The accordion pleating can be in the form of a plurality of substantially straight, substantially parallel rows, or it can be in the form of a continuous spiral, or any combination thereof, so that the accordion pleating allows the shaft to bend in all three dimensions.

The spiral spring can be inserted within a flexible region of the shaft can be attached to the shaft, preferably on its interior, or can be embedded within the shaft material. It can be made of metal, plastic, glass fiber, carbon fiber, any combination thereof, or of any other suitable material as is known in the art. The plastic can be polycarbonate, plastic composites, Ultem® polyetherimide resin or any other suitable plastic as is known in the art, The spiral spring is firmly attached to the device at both ends, preferably to the collector head at its distal end and to the knob, shaft or other rotation mechanism at the proximal end, so that the spring enables the collector head to bend in all three directions (providing the same with at least 3 degrees of freedom), thereby allowing it to follow the tortuosity of the ear canal.

In preferred embodiments, in the device's undeformed configuration, the main longitudinal axis of the spiral spring is collinear with the main longitudinal axis of the collector head.

It is a core concept behind the present invention is to provide a simple mechanical device for cerumen removal.

It is another core concept of the invention is that soft cerumen is amassed in or on the device by mechanical action of at least a portion of the device and that the amassed cerumen is removed, with the device, from the ear.

All of the above are merely examples of embodiments of the core concepts. Any combination of the above examples remains within the scope of the invention.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A method for mechanically removing cerumen from an ear canal, comprising:
   providing a cerumen removal apparatus for mechanically removing the cerumen from the ear canal, comprising: a device body having a distal end and a proximal end interconnected by a main longitudinal axis; said device body distal end comprising a collector head having an outer surface, an inner surface enclosing a lumen, and a distal tip ending with a front surface enclosing an opening opened to said lumen for amassing the cerumen in said lumen via said opening, said collector head including at least one spiral vane or ridge projecting radially inwardly from said inner surface in said lumen and configured to guide the cerumen in a proximal direction into said collector head when said collector head rotates in the ear canal in accordance with direction of said at least one spiral vane or ridge; and said device body proximal end comprises at least one rotating mechanism in a form of a knob and adapted to rotate said collector head;

emplacing said cerumen removal apparatus in the ear canal; and rotating said rotating mechanism, thereby amassing the cerumen, so as to remove the cerumen from the ear canal.

2. The method according to claim 1, wherein said emplacing includes positioning sides or/and edges of said collector head adjacent to wall of the ear canal, and wherein said rotating includes scraping the ear canal wall with said sides or/and edges of said collector head.

3. The method according to claim 1, further comprising decoupling said rotating mechanism, thereby extending said collector head in the ear canal no more than a predetermined distance.

\* \* \* \* \*